United States Patent
Purdy et al.

(10) Patent No.: US 11,304,739 B2
(45) Date of Patent: Apr. 19, 2022

(54) CEMENT MIXING AND INJECTION SYSTEM AND METHODS

(71) Applicant: DFine, Inc., South Jordan, UT (US)

(72) Inventors: Craig Purdy, Sunnyvale, CA (US); Dan Balbierz, Redwood City, CA (US); Nate Shirley, Pleasant Grove, UT (US); Andy Poursaid, Sandy, UT (US); Gregory R. McArthur, Sandy, UT (US); Robert D. Poser, Scotts Valley, CA (US)

(73) Assignee: DFine, Inc., South Jordan, UT (US)

( * ) Notice: Subject to any disclaimer, the term of this patent is extended or adjusted under 35 U.S.C. 154(b) by 156 days.

(21) Appl. No.: 16/053,011

(22) Filed: Aug. 2, 2018

(65) Prior Publication Data

US 2019/0038331 A1 Feb. 7, 2019

Related U.S. Application Data

(66) Substitute for application No. 62/540,766, filed on Aug. 3, 2017.

(51) Int. Cl.
*A61B 17/88* (2006.01)
*B01F 5/00* (2006.01)
(Continued)

(52) U.S. Cl.
CPC ...... *A61B 17/8833* (2013.01); *A61B 17/8819* (2013.01); *A61B 17/8822* (2013.01);
(Continued)

(58) Field of Classification Search
CPC ............ A61B 17/8833; A61B 17/8819; A61B 17/8822; A61B 17/8802; A61B 17/8825;
(Continued)

(56) References Cited

U.S. PATENT DOCUMENTS

| | | | | |
|---|---|---|---|---|
| 4,386,606 | A | * | 6/1983 | Tretinyak .......... A61M 5/31501 604/220 |
| 5,090,962 | A | * | 2/1992 | Landry, Jr. ......... A61M 5/31511 604/110 |

(Continued)

FOREIGN PATENT DOCUMENTS

| | | |
|---|---|---|
| CN | 205007022 | 2/2016 |
| EP | 1466572 | 10/2004 |

(Continued)

OTHER PUBLICATIONS

International Search Report and Written Opinion dated Nov. 19, 2018 for PCT/US2018/044984.
European Search Report dated May 26, 2021 for EP18842076.4.

*Primary Examiner* — Marcela I. Shirsat
(74) *Attorney, Agent, or Firm* — Stoel Rives LLP

(57) ABSTRACT

The present disclosure relates to systems and methods for mixing and injecting fluid treatment, such as cement to treat bone or hard tissue. In some embodiments, a mixing apparatus may facilitate mixing within a syringe. Additionally, the syringe may be configured to extract bone cement from a cement mixer. A syringe for mixing and injecting cement may include a detachable handle that may be detached after extracting bone cement from a mixer to facilitate coupling to a high-pressure syringe for injection.

19 Claims, 21 Drawing Sheets

(51) Int. Cl.
*A61B 17/00* (2006.01)
*A61M 5/315* (2006.01)
*A61M 5/31* (2006.01)
*B01F 15/02* (2006.01)

(52) U.S. Cl.
CPC ............ *B01F 5/00* (2013.01); *A61B 17/8802* (2013.01); *A61B 17/8825* (2013.01); *A61B 2017/0046* (2013.01); *A61B 2017/00477* (2013.01); *A61B 2017/8838* (2013.01); *A61M 5/31501* (2013.01); *A61M 5/31511* (2013.01); *A61M 5/31515* (2013.01); *A61M 2005/3139* (2013.01); *A61M 2005/31508* (2013.01); *B01F 15/0278* (2013.01)

(58) Field of Classification Search
CPC .... A61B 2017/0046; A61B 2017/8838; A61B 2017/8813; B01F 7/00; B01F 13/0023; B01F 15/00506; B01F 15/0278; A61M 5/31501; A61M 5/31511; A61M 5/31515; A61M 5/502; A61M 5/315; A61M 5/347; A61M 2005/31508; A61M 2005/3139; A61M 2005/2073
USPC ............................................. 606/94; 604/220
See application file for complete search history.

(56) References Cited

U.S. PATENT DOCUMENTS

| | | | |
|---|---|---|---|
| 8,348,494 | B2 | 1/2013 | Melsheimer et al. |
| 9,326,914 | B2* | 5/2016 | Anitua Aldecoa ... A61B 5/1438 |
| 9,545,464 | B2* | 1/2017 | Roche ................. A61M 1/0009 |
| 2005/0113843 | A1 | 5/2005 | Arramon |
| 2006/0083769 | A1 | 4/2006 | Kumar et al. |
| 2006/0235354 | A1 | 10/2006 | Kaal et al. |
| 2009/0198242 | A1* | 8/2009 | Truckai ............... A61B 17/8822 606/93 |
| 2011/0160737 | A1* | 6/2011 | Steffen ............... A61B 17/8822 606/94 |
| 2012/0083789 | A1* | 4/2012 | Blakemore ........ A61B 17/8833 606/93 |
| 2014/0350516 | A1* | 11/2014 | Schwab ............ A61M 5/31526 604/506 |
| 2015/0314120 | A1* | 11/2015 | Gardner ................ A61M 39/16 206/210 |

FOREIGN PATENT DOCUMENTS

| | | |
|---|---|---|
| EP | 3159028 | 4/2017 |
| WO | 2014047030 | 3/2014 |

* cited by examiner

US 11,304,739 B2

CEMENT MIXING AND INJECTION SYSTEM AND METHODS

RELATED APPLICATIONS

This application claims priority to U.S. Provisional Application No. 62/540,766, filed on Aug. 3, 2017 and titled "Cement Mixing And Injection System And Methods" which is hereby incorporated by reference in its entirety.

TECHNICAL FIELD

The present disclosure relates to systems and methods for mixing and injecting cement to treat bone or hard tissue.

BRIEF DESCRIPTION OF THE DRAWINGS

The written disclosure herein describes illustrative embodiments that are non-limiting and non-exhaustive. Reference is made to certain of such illustrative embodiments that are depicted in the figures.

DETAILED DESCRIPTION

Figure 1:
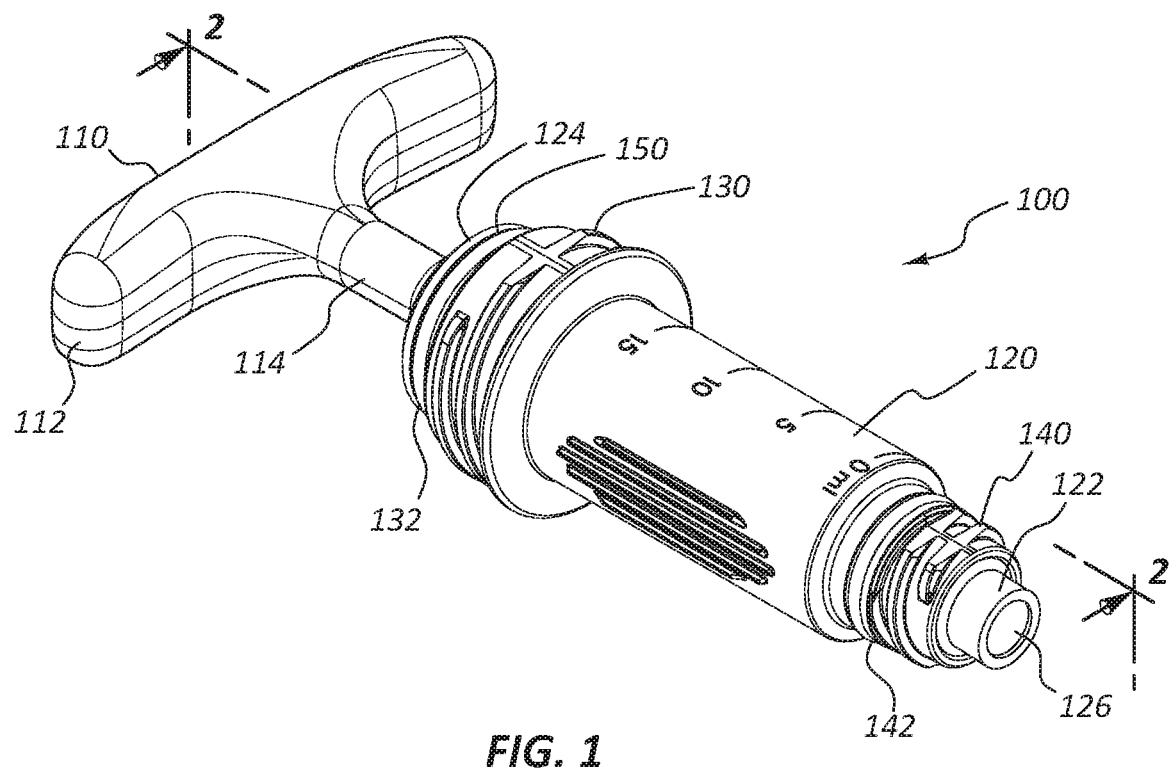
FIG. 1 illustrates a perspective view of a multi-interface syringe to aspirate and deliver cement from a mixing vessel to a hard tissue, according to one embodiment.

This disclosure describes systems and methods for mixing and injecting cement to treat bone or hard tissue. In some embodiments, a syringe with multiple interfaces (multi-interface syringe) may facilitate aspiration of a fluid treatment, such as bone cement from a mixer and delivery of the bone cement to hard tissue using a pressure delivery device. In some embodiments, a high-pressure syringe may facilitate aspiration of bone cement and provide sufficient force to push bone cement through a length of tubing for delivery. In some embodiments, a syringe may include an internal mixing apparatus to mix bone cement powder and a liquid monomer within the syringe.

Various medical procedures may utilize a cement to improve the strength and rigidity of a bone or joint. For example, when treating spine fractures, a practitioner may inject cement into vertebral cavities. In some instances, the cement is formed by combining a powder and a liquid in a mixing vessel. Once fully mixed, the cement is transferred from the mixing vessel to a dispensing member.

The process of mixing the cement may be unpleasant for a practitioner. For example, while mixing the cement, a practitioner may be exposed to an offensive, noxious odor. Further, removal of the cement from the mixing vessel into the dispensing member using traditional methods may be cumbersome and/or messy.

Additional challenges may be presented when a practitioner delivers the cement to a patient. For instance, the cement may have a high viscosity, which may in turn necessitate a practitioner applying a large amount of force to the dispensing member to deliver the cement. Further, because the work exerted to deliver the cement increases as the distance the cement is pushed along a delivery line increases, some systems may minimize this distance, thus requiring a practitioner to apply the force at or near the delivery site. However, working near a delivery site may be undesirable. For example, during certain procedures the delivery site may be exposed to electromagnetic radiation for imaging. If a practitioner works near the delivery site, the practitioner may obscure the imaging and/or be exposed to dangerous radiation.

Embodiments described herein may alleviate the challenges of mixing, extracting, and delivering cement. For example, a multi-interface syringe may facilitate delivery of the bone cement from a distance by providing an interface for a pressure delivery device. Additionally, a high-pressure syringe may facilitate aspiration of bone cement and provide sufficient force to push bone cement through a length of tubing for delivery. In some embodiments, a syringe may include an internal mixing apparatus to mix bone cement within the syringe, reducing practitioner exposure to the cement's odor and eliminating the need to withdraw the cement from a separate mixing vessel.

Notwithstanding specific examples disclosed herein reciting the mixing or delivery of bone cement, mixing and/or delivery of a wide variety of compounds is within the scope of this disclosure. For example, the systems and methods described herein may be configured to deliver and/or mix medicaments, contrast agents, fluids configured to inflate one or more medical devices, and so forth. Materials may be mixed and/or delivered as gasses, liquids, suspensions, solutions, and any other material sufficient flowable to be advanced through a tube.

The phrase "coupled to" is broad enough to refer to any suitable coupling or other form of interaction between two or more entities, including mechanical, fluidic and thermal interaction. Thus, two components may be coupled to each other even though they are not in direct contact with each other. The phrase "attached to" refers to interaction between two or more entities which are in direct contact with each other and/or are separated from each other only by a fastener of any suitable variety (e.g., mounting hardware or an adhesive). The phrases "selectively coupled to" and "selectively attached to" refer to interactions between two or more entities which may be detached or coupled/attached.

"Axial displacement" refers to movement in a longitudinal direction of an elongated member. "Rotational displacement" refers to a change in angle of an elongated member about an axis of rotation.

The terms "proximal" and "distal" are opposite directional terms. As used herein, the distal end of a device or component is the end of the component that is furthest from the physician during ordinary use. The proximal end refers to the opposite end, or the end nearest the physician during ordinary use.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIG. 1 illustrates a perspective view of a multi-interface syringe 100 to aspirate and deliver cement from a mixing vessel to a hard tissue, according to one embodiment. More specifically, in some procedures, the multi-interface syringe 100 provides a means to transfer mixed bone cement from a mixing system into a syringe barrel which then can be connected to a delivery needle and a pressure delivery device to deliver the cement into fractured vertebra or other hard tissue. The multi-interface syringe 100 may include a releasable handle 110, a barrel 120, a plunger within the barrel, and a retainer 150.

The barrel 120 may be an elongate hollow body comprising a sidewall forming a reservoir with a proximal open end 124 and a distal aperture. The reservoir may receive and store bone cement. For example, a practitioner may aspirate cement through a distal aperture 126 by pulling on the releasable handle 110. The releasable handle 110 may be selectively coupled to the plunger within the barrel 120. Thus, as the releasable handle 110 is pulled, the plunger moves toward the retainer 150.

The barrel 120 may comprise a tapered nose 122 and multiple adapter interfaces (e.g., 130 and 140). The tapered nose 122 may facilitate an interference fit with a similarly tapered side port of a mixing vessel. The adapter interfaces (e.g., 130 and 140) may facilitate interactions with additional delivery tools.

The first interface 140 may selectively couple with a delivery needle. In some embodiments, the first interface 140 may attach directly to a delivery needle. In some embodiments, the first interface 140 may attach to a coupler that attaches to the delivery needle. The coupler may be a swivel elbow that allows the multi-interface syringe 100 to rotate about the delivery needle. A first seal 142 may prevent cement from leaking through a coupling of a tool to the first interface 140.

The second interface 130 may selectively couple with a pressure delivery device when the releasable handle 110 is removed from the plunger. In some embodiments, the second interface 130 may attach directly to the pressure delivery device. In some embodiments, the second interface 130 may attach to an adapter that couples with the pressure delivery device. The adapter may include a length of tubing that allows a practitioner to deliver the cement from a distance. A second seal 132 may prevent cement from leaking through a coupling of a tool to the second interface 130.

The retainer 150 may be coupled to a proximal end of the barrel 120 and prevent the plunger from being pulled through the proximal open end 124. The retainer 150 may also limit the rotational movement of the plunger relative to the barrel 120. Thus, the retainer 150 may limit both axial and rotational displacement of the plunger when the plunger is near the proximal end of the barrel 120.

The releasable handle 110 may couple to and uncouple from the plunger. The releasable handle 110 may include a hand grip 112 and an elongate shaft 114. The hand grip 112 may provide a hold for a practitioner. The elongate shaft 114 may extend into the barrel 120 and selectively couple with the plunger. In some embodiments, a trigger may facilitate the release of the elongate shaft 114 from the plunger. In some embodiments, a practitioner may uncouple the releasable handle 110 by pulling the plunger to the retainer 150 and rotate the releasable handle 110.

Figure 2:
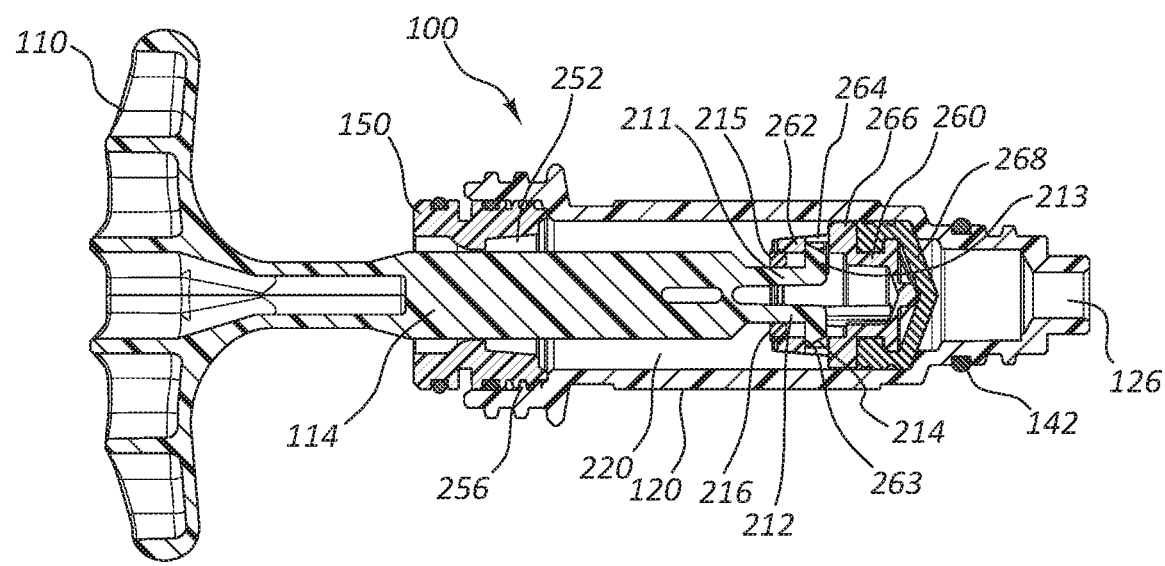
FIG. 2 illustrates a cross-sectional view of the multi-interface syringe of FIG. 1.

FIG. 2 illustrates a cross-sectional view of the multi-interface syringe 100 of FIG. 1. As also described above, a plunger 260 within the barrel 120 may move to draw or expel bone cement. A practitioner may move the plunger 260 within a reservoir 220 of the barrel 120 using either the releasable handle 110 or a pressure delivery device when the releasable handle 110 is detached.

As shown, the plunger 260 may include a seal 268 and a plunger body 266. The seal 268 may prevent or minimize aspirated material from leaking behind the plunger 260. The seal 268 may be coupled to the body 266. The body 266 may provide structure and be shaped to allow axial and rotational displacement of the plunger 260 within the barrel 120. The body 266 may include a mating proximal portion or a mating feature, such as multi-faceted proximal portion 262 and mating slots 263, 264. The multi-faceted proximal portion 262 may be formed from sidewalls with multiple planes on the exterior. The mating slots 263, 264 may be formed in the sidewalls of the multi-faceted proximal portion 262. The mating slots 263, 264 may extend through the sidewalls and facilitate coupling between the releasable handle 110 and the plunger 260.

The releasable handle 110 may comprise a set of arms, such as flexures 211, 212 at a distal end of the elongate shaft 114. The flexures 211, 212 may be two or more prongs/flexible arms positioned around a longitudinal axis of the releasable handle 110 and configured to flex toward the longitudinal axis of the releasable handle 110. In some embodiments, the flexures 211, 212 may be made of the same material as the elongate shaft 114. The flexibility of the flexures 211, 212 may be partially dependent on their dimensions. For example, as shown the flexures 211, 212 are narrow in comparison to the elongate shaft 114. This configuration may provide a stiff elongate shaft 114 and bendable flexures 211, 212 formed from a single material.

Each of the flexures 211, 212 may include a boss 215, 216 and a protrusion 213, 214. The flexure bosses 215, 216 may be features that extend from the flexures 211, 212 and make contact with the interior sidewall of the multi-faceted proximal portion 262 of the plunger 260. The contact between the flexure bosses 215, 216 and the plunger 260 may stabilize the releasable handle 110. The protrusions 213, 214 may extend radially from the flexures 211, 212 and be configured to enter the mating slots 263, 264 to interlock the releasable handle 110 and the plunger 260.

The retainer 150 may be coupled to the proximal end of the barrel 120 and include a socket 252 to receive the plunger 260. The retainer 150 may be coupled to the barrel 120 via a threaded interface 256. In some embodiments, the retainer 150 may be bonded to the barrel 120 to prevent separation. The socket 252 may have a mating portion, such as a multi-faceted interior surface. The multi-faceted proximal portion 262 may dock within the socket 252. To facilitate docking, the socket 252 and the multi-faceted proximal end 262 of the plunger 260 may be tapered.

The multiple planes of the socket 252 and the multi-faceted proximal end 262 may prevent the plunger 260 from rotating with respect to the socket 252 when docked. This may allow the releasable handle 110 to release from the plunger 260 via a rotational force. For example, when the plunger 260 is seated within the retainer 150 and the releasable handle 110 is rotated relative to the plunger 260, the flexures 211, 212 may bend toward the longitudinal axis of the releasable handle 110, releasing the protrusions 213, 214 from the mating slots 263, 264. Without the protrusions 213, 214 interlocking with the mating slots 263, 264, a practitioner may pull the releasable handle 110 from the plunger 260. As further detailed herein, this may then allow a physician to use another tool, such as a pressure delivery device, to deliver cement.

Figure 3A:
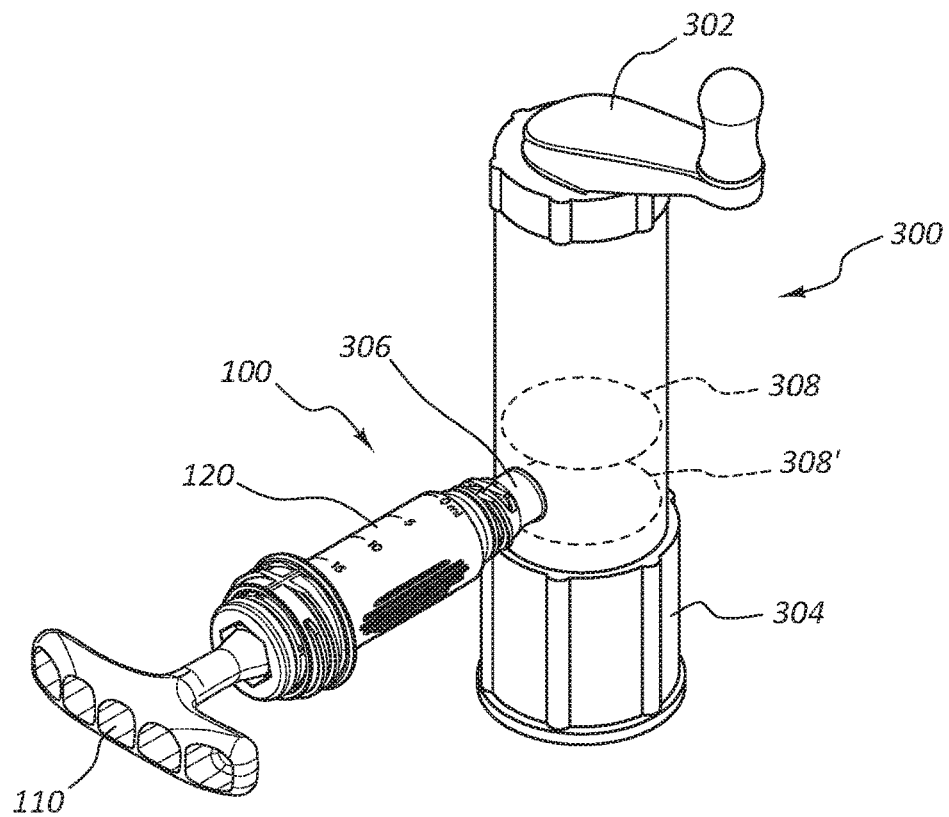
FIG. 3A illustrates the multi-interface syringe of FIG. 1 interfacing with a mixing system, according to one embodiment.
Figure 3B:
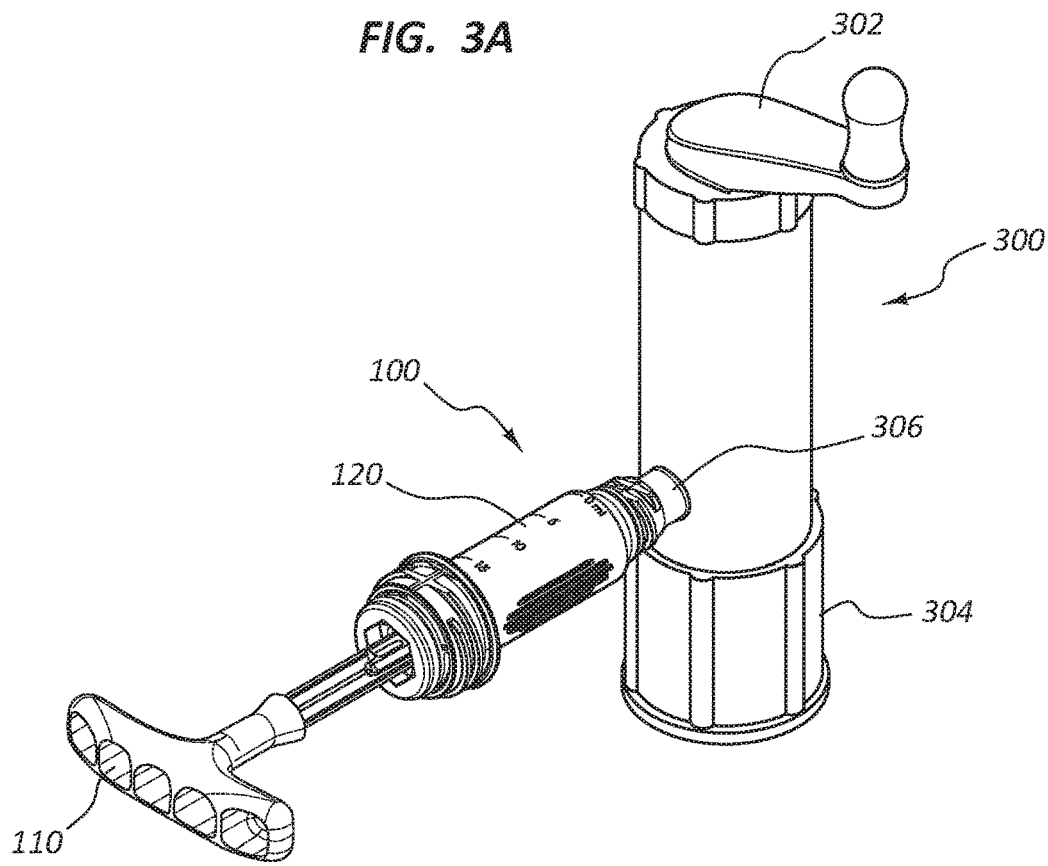
FIG. 3B illustrates the multi-interface syringe and mixing system of FIG. 3A with the releasable handle of the multi-interface syringe drawn back.

FIGS. 3A and 3B illustrate the multi-interface syringe 100 of FIG. 1 aspirating bone cement from a mixing system 300, according to one embodiment. Specifically, FIG. 3A illustrates the multi-interface syringe 100 interfacing with the mixing system 300, and FIG. 3B illustrates the multi-interface syringe 100 with the releasable handle 110 drawn back.

To create cement, the practitioner may pour dry cement powder into the mixing system 300 and add a liquid monomer. For example, in some embodiments, Teknimed's Opacity+Vertebroplasty Bone Cement may be used to create a cement. The user may then prepare the cement for use by rotating a handle 302 to mix the cement powder and monomer, in some embodiments the materials used may specify a mixing time, for example a one minute mixing time may be indicated for certain cements. Others may be mixed for different durations, such as at least 1 minute, 2 minutes, three minutes, about five minutes, and so forth.

In some embodiments, the mixing system 300 has a movable floor 308 adjustable via a floor actuator 304. The movable floor 308 is in a raised position during mixing, to prevent or minimize leakage of cement through the tapered side access port 306 during mixing of the cement. The movable floor 308 seals off the tapered side access port 306 in this raised position shown as element 308.

To transfer the cement, the practitioner inserts the tapered nose of the multi-interface syringe 100 into the side port 306 of the mixing system 300. The tapered shape of the nose of the multi-interface syringe 100 and the side port 306 provide a snug interference fit. With the multi-interface syringe 100 in position, the practitioner may lower the movable floor 308' via the floor actuator 304, allowing the cement to flow into the multi-interface syringe 100. While there is only one movable floor 308, two different positions that the movable floor 308 may be placed in are designated herein as element 308 (raised) and 308' (lowered).

As shown in FIG. 3B, the releasable handle 110 of the multi-interface syringe 100 is drawn back (with the movable floor 308' positioned to provide communication between cement in the mixing system 300), bone cement may be transferred from the mixing system 300 into the barrel 120 of the multi-interface syringe 100. The releasable handle 110 pulls a plunger within the barrel 120 to create a low pressure chamber to draw the cement from the mixing system 300.

In the fully drawn back position the releasable handle 110 can quickly be detached from the multi-interface syringe 100. For example, in some embodiments, a counter-clockwise rotation (quarter turn) may cause the releasable handle 110 to detach. As explained in more detail with reference to FIGS. 4-9 below, the interaction between the distal end of the releasable handle 110, the retainer, and the plunger may facilitate the detachment.

Figure 4:
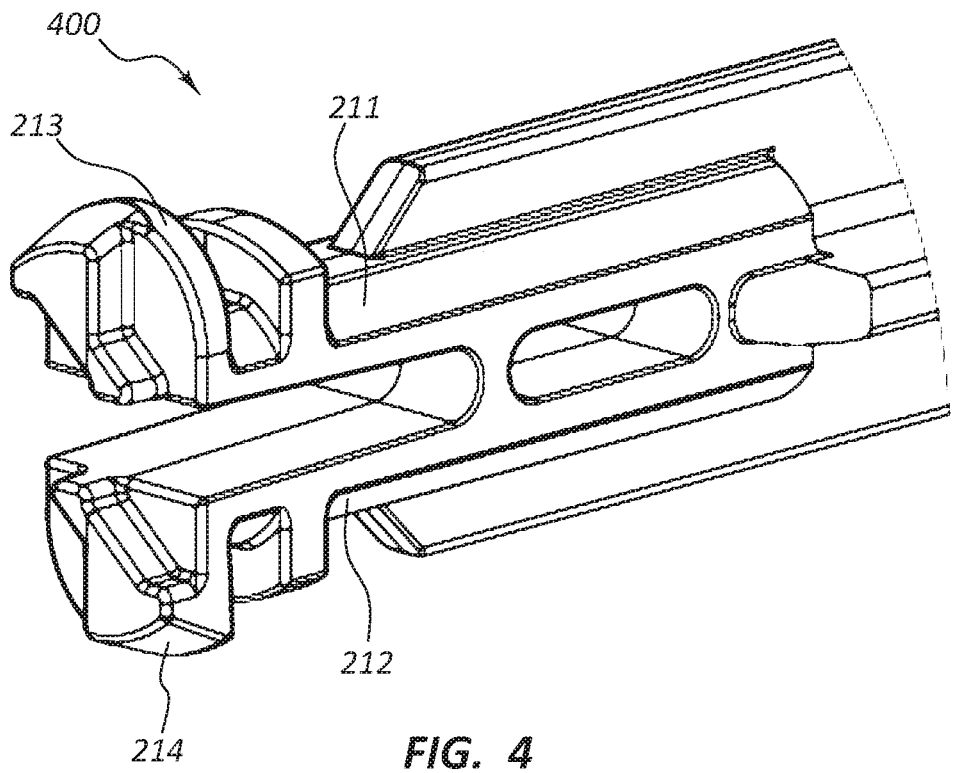
FIG. 4 illustrates a distal end of a releasable handle of the multi-interface syringe of FIG. 1.

FIG. 4 illustrates a distal end 400 of the releasable handle 110 of FIG. 1, according to one embodiment. The distal end 400 is capable of flexing inward which essentially reduces the nominal diameter of a circle around the deflected portions. The distal end 400 may include two flexures 211, 212 that are spaced around the axis of the releasable handle. Each flexure may include a protrusion 213, 214 for coupling to a plunger. Each protrusion 213, 214 may comprise a rounded edge to interact with an inner edge of a mating slot in a plunger and facilitate rotation of the handle relative to the plunger. For instance, when the handle is rotated relative to the plunger, the sidewalls of the plunger interact with the protrusions 213, 214 and cause the arms to flex toward the longitudinal axis of the handle to facilitate removal of the handle from the plunger.

Figure 5:
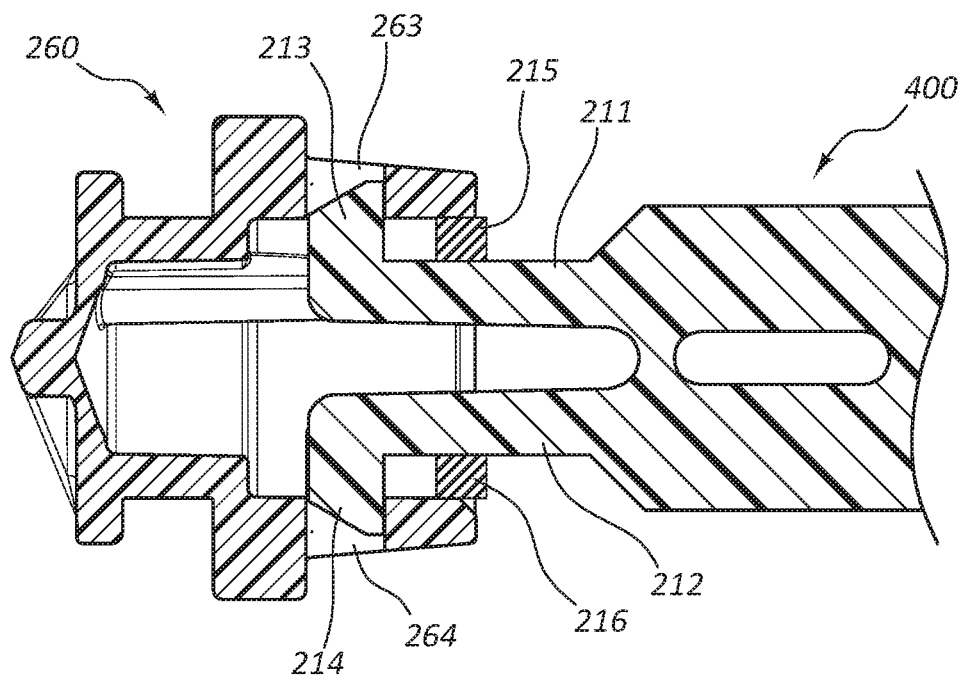
FIG. 5 illustrates a cross-sectional view of a distal end of the releasable handle of FIG. 1 coupled to a plunger, according to one embodiment.

FIG. 5 illustrates a distal end 400 of the releasable handle 110 of FIG. 1 coupled to the plunger 260, according to one embodiment. When the distal end 400 is connected to the plunger 260, the flexures 211, 212 are in a resting position. In some embodiments, the resting position is the width of the flexures 211, 212 without a force applied to them. A pair of mating slots 263, 264 in the plunger 260 provide an open area for the over-hanging diameters, protrusions 213, 214, of the flexures 211, 212 to reside in. This arrangement interlocks the two components together. In this state, a practitioner can push, pull and rotate the plunger 260 by applying force to the hand-grip portion of the releasable handle. The bosses 215, 216 provide stability for the releasable handle while in the plunger 260.

To remove the releasable handle, the flexures 211, 212 are positioned around a longitudinal axis of the handle and configured to bend toward the longitudinal axis of the handle. For example, in one embodiment, a trigger on the hand-grasp of the releasable handle may pull the flexures 211, 212 together. In some embodiments, when the releasable handle is rotated relative to the plunger 260 (with the plunger 260 locked or seated such that it does not rotate with the releasable handle, as further detailed below) the plunger 260 forces the flexures 211, 212 together.

Figure 6:
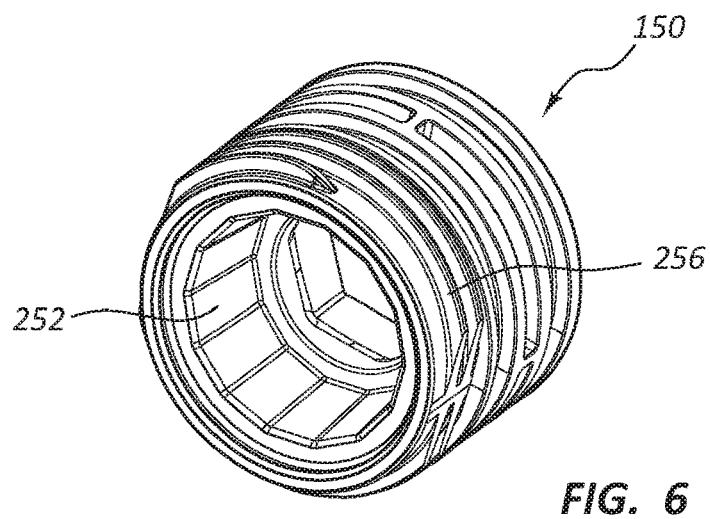
FIG. 6 illustrates a perspective view of a retainer of the multi-interface syringe of FIG. 1, according to one embodiment.

FIG. 6 illustrates a perspective view of the retainer 150 of the multi-interface syringe of FIG. 1, according to one embodiment. The retainer 150 may include the threaded interface 256 and the socket 252. The threaded interface 256 may facilitate coupling of the retainer 150 to the barrel of the multi-interface syringe. The socket 252 may limit the rotation of a plunger seated within the socket 252.

The threaded interface 256 may be configured to remain coupled to the barrel of the multi-interface syringe when a practitioner rotates a releasable handle coupled to a plunger seated in the socket 252. For example, in one embodiment, the threaded interface 256 may be left-handed, and the rotation of the releasable handle may be limited to the opposite direction. In some embodiments, the threaded interface 256 may be bonded to the barrel of the multi-interface syringe.

The socket 252 may include a tapered recess with multiple facets. The multiple facets may be keyed to the plunger. For example, in some embodiments the socket 252 and the plunger may include 14 facets or planes. Other embodiments may comprise more or less facets, such as 3-20 facets or more, and any range therein. As the user draws the plunger back or proximally by pulling on the hand-grip portion of the releasable handle, the proximal end of the plunger engages the tapered recess of the socket 252. The tapering and the multiple facets facilitate alignment of the plunger and the socket 252. Embodiments with a greater number of facets may facilitate ease of alignment. The tapering provides gradual engagement as the practitioner draws the plunger towered the socket 252.

Figure 7:
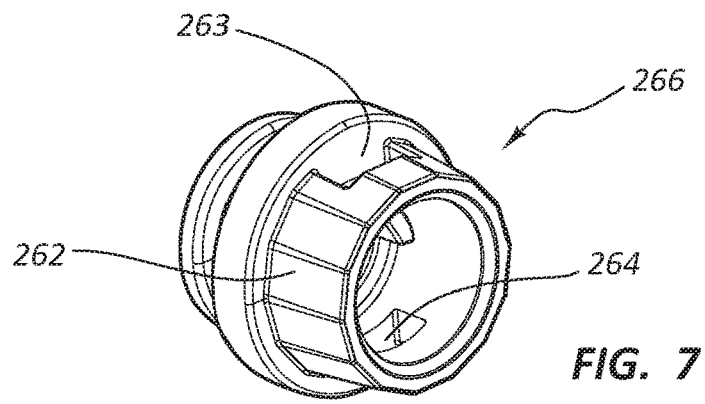
FIG. 7 illustrates a perspective view of a plunger of the multi-interface syringe of FIG. 1, according to one embodiment.

FIG. 7 illustrates a perspective view of a plunger body 266 of the multi-interface syringe 100 of FIG. 1, according to one embodiment. The plunger body 266 may include a multi-faceted proximal portion 262 and the mating slots 263, 264. The facets of the multi-faceted proximal portion 262 may correspond to the facets on the retainer 150. If the components are slightly out of perfect alignment the taper and the faceted geometries serve to self-align the parts.

As shown, the multi-faceted proximal portion 262 may be hollow to accept a releasable handle. The mating slots 263, 264 may be configured to accept the distal end of the releasable handle. In some embodiments, as shown, the mating slots 263, 264 may extend through the multi-faceted proximal portion 262; in other embodiments, the mating slots 263, 264 may only extend through a portion of the plunger body 266, providing grooves to house the releasable handle.

Figure 8:
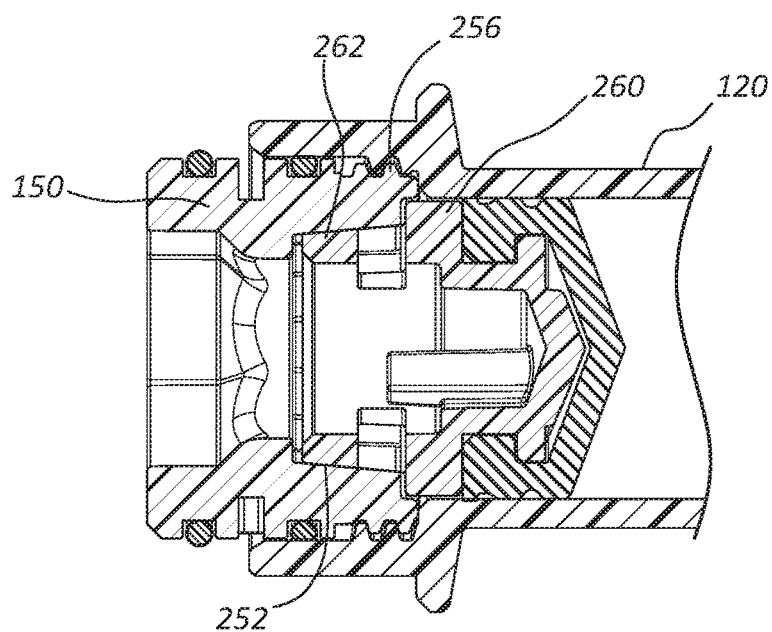
FIG. 8 illustrates the plunger of FIG. 7 docked within a retainer of the multi-interface syringe of FIG. 1, according to one embodiment.

FIG. 8 illustrates the plunger 260 docked within the retainer 150 of the multi-interface syringe 100 of FIG. 1, according to one embodiment. Once the two parts are "docked" (fully seated with each other), the plunger 260 can no longer rotate with respect to the retainer 150 due to the faceted surface interlocking the two parts. The retainer 150 may be threaded into the barrel 120 (possibly bonded as well), preventing the retainer 150 from rotating with respect to the barrel 120, thereby preventing the plunger 260 from rotating with respect to the barrel 120 when docked. The threaded interface 256 may be left-hand threaded to prevent the retainer 150 from unthreading when the releasable handle is rotated counter-clockwise. Thus, when the plunger 260 is not docked, rotation of the releasable handle (110 of FIG. 1) with respect to the barrel 120 may also rotate the plunger 260, due to the interaction of the distal end of the releasable handle (400 of FIG. 4) and the plunger 260 as described above. Docking of the plunger 260 and the retainer 150 may prevent rotation of the plunger 260 with respect to the retainer 150 and provide stability for decoupling of the distal end of the releasable handle (400 of FIG. 4) and the plunger 260 as detailed below.

Figure 9:
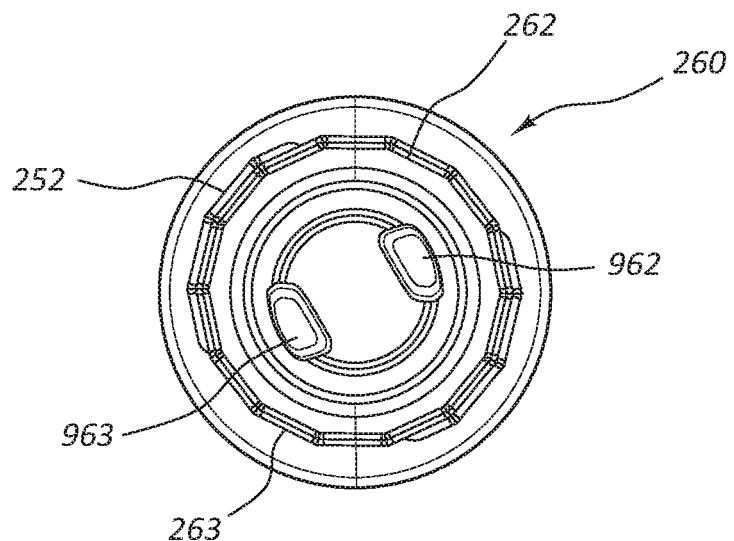
FIG. 9 illustrates a planar view of the multi-faceted proximal portion of the plunger of FIG. 7, according to one embodiment.

FIG. 9 illustrates a planar view of the multi-faceted proximal portion 262 of the plunger 260 of FIG. 2, according to one embodiment. As shown, the plunger 260 may comprise two bosses 962, 963 within a chamber of the multi-faceted proximal portion 252. The two bosses 962, 963 may be located at or near the right side of each of the mating slots 262, 263 to prevent the releasable handle from being rotated clockwise.

Figure 10A:
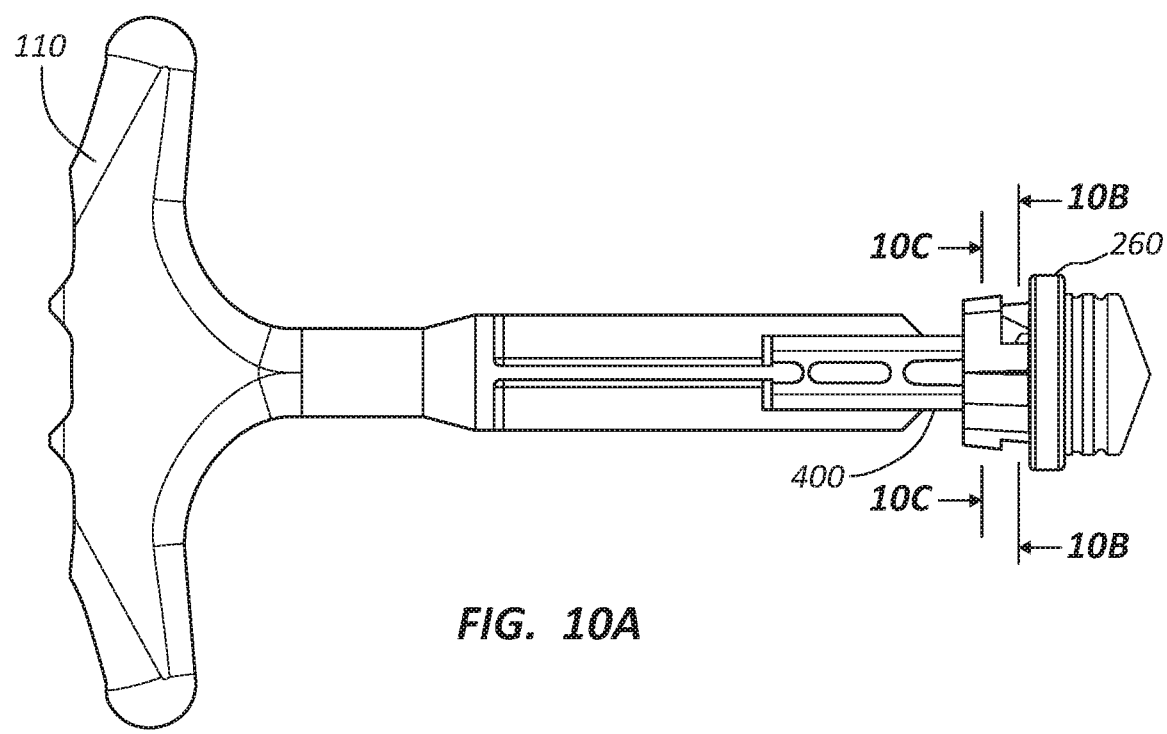
FIG. 10A illustrates a side view of the releasable handle coupled to the plunger.
Figure 10B:
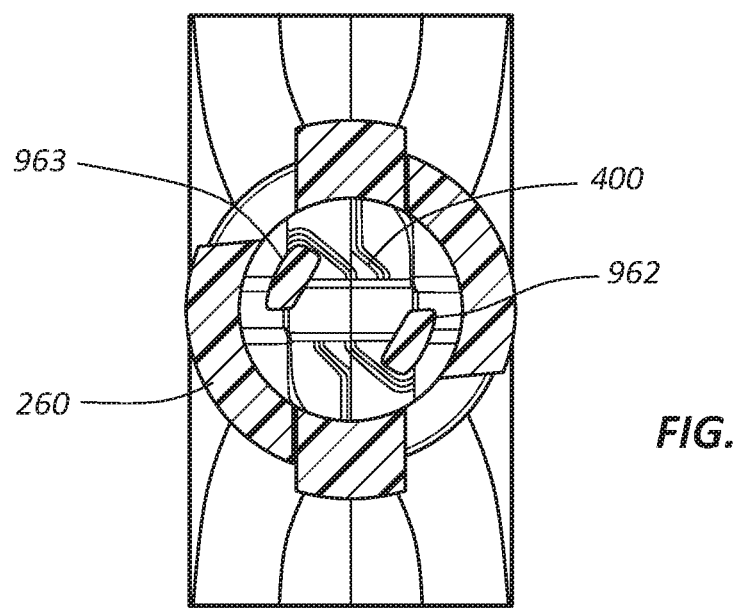
FIG. 10B illustrates a cross-sectional view illustrating the bosses in the plunger interacting with the distal end of the releasable handle.
Figure 10C:
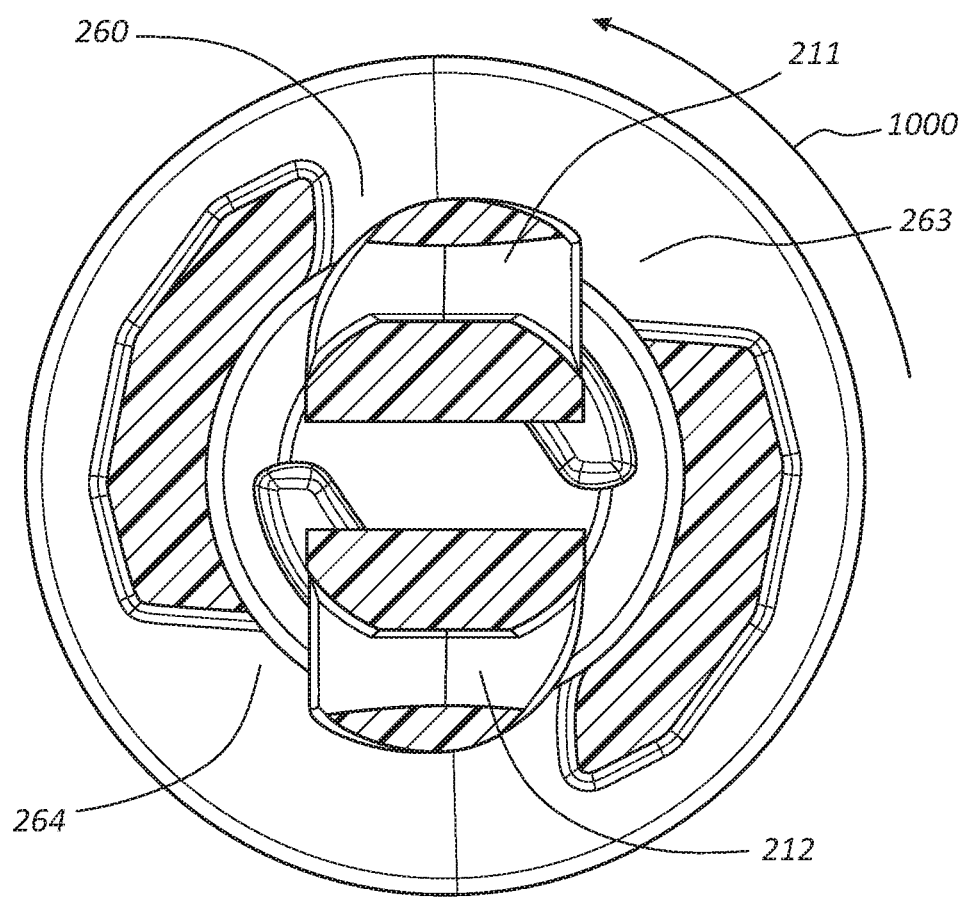
FIG. 10C illustrates a cross-sectional view of the flexures interacting with the mating slots.

FIGS. 10A, 10B, and 10C illustrate various views of the releasable handle 110 of FIG. 1 coupled to the plunger 260. Specifically, FIG. 10A illustrates a side view of the releasable handle 110 coupled to the plunger 260, and FIGS. 10B and 10C illustrate cross-sectional views of the releasable handle 110 as marked in FIG. 10A. When coupled, the releasable handle 110 may be used to manipulate the position of the plunger 260.

FIG. 10B illustrates a cross-sectional view illustrating the bosses 962, 963 in the plunger 260 interacting with the distal end 400 of the releasable handle 110. When the releasable handle 110 is connected to the plunger 260, the bosses 962, 963 prevent the releasable handle 110 from rotating clockwise with respect to the plunger 260, unless the flexures 211, 212 are deflected during decoupling of the plunger 260 from the releasable handle 110. The bosses 962, 963 may provide a hard stop between the plunger 260 and the releasable handle 110 when the flexures are not deflected. However, as detailed below, in some embodiments, the bosses 962, 963 may deflect slightly to prevent the flexures 211, 212 from breaking. For example, the bosses 962, 963 may be formed from a flexible material with sufficient resilience to prevent the releasable handle 110 from rotating clockwise while providing a cushion for the flexures 211, 212.

FIG. 10C illustrates a cross-sectional view of the flexures 211, 212 interacting with the mating slots 263, 264. A counter-clockwise rotation 1000 with respect to the plunger may drive the large radius of the flexures 211, 212 into the radius on the inner edges of the side windows of the plunger 260. The interaction may squeeze the flexures 211, 212 together. A rounded edge on the flexures 211, 212 may provide a surface to interact with the sidewalls. The gradual slope of the rounded edge may define the rate at which the flexures 211, 212 squeeze together. When the operator rotates the releasable handle 110 counter-clockwise and deflects the flexures in to allow rotation of the handle with respect to the plunger such that the plunger and handle are aligned in a release position, then pulls on the releasable handle 110, the releasable handle 110 is removed from the plunger 260 and exits the proximal end of the barrel 120.

Figure 11:
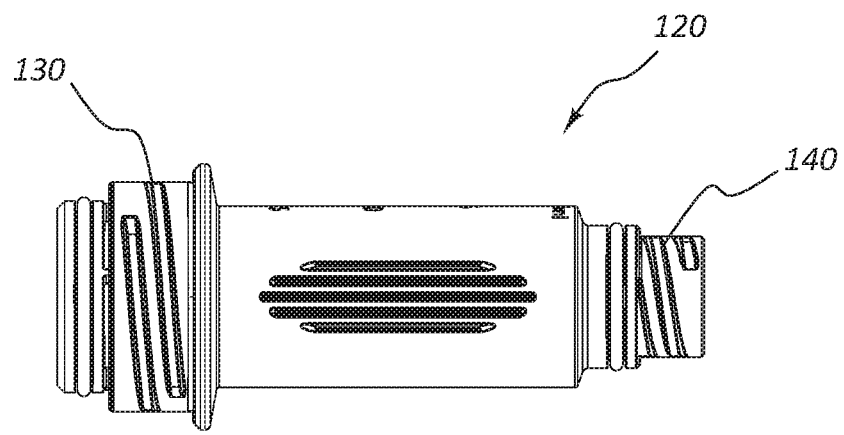
FIG. 11 illustrates a side view of a barrel of the multi-interface syringe of FIG. 1 with the releasable handle removed, according to one embodiment.

FIG. 11 illustrates a side view of the barrel 120 of FIG. 1 with the releasable handle 110 removed, according to one embodiment. These interfaces may be adapted to interface with a variety of medical devices. For example, a first interface 140 may be configured to connect with a swivel elbow, and a second interface 130 may be configured to connect with a pressure delivery device. In some embodiments, the interfaces can comprise a high-pitch thread. For example, the pitch of the thread may allow devices to be coupled to the barrel with approximately a quarter turn facilitating rapid coupling of the components.

Figure 12:
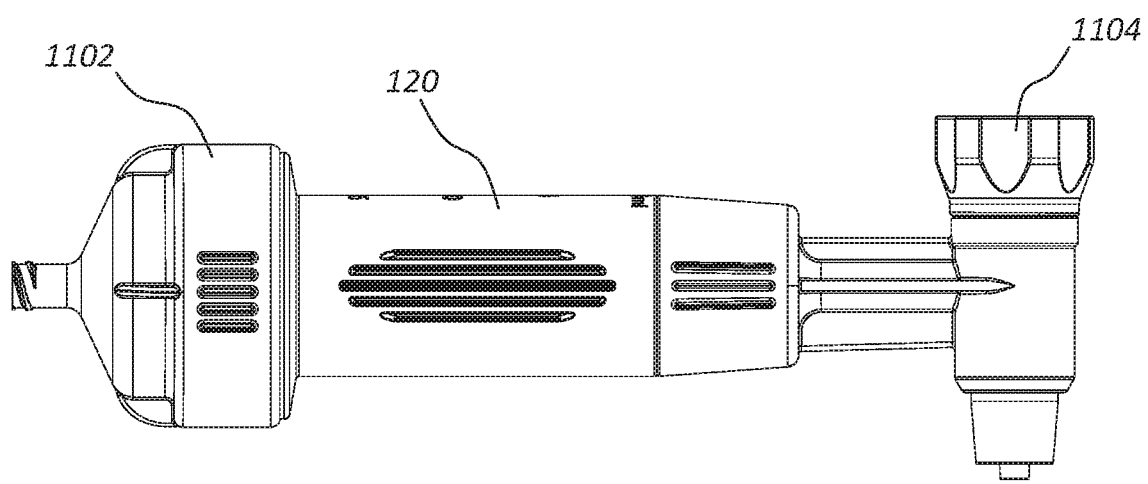
FIG. 12 illustrates a side view of the barrel of FIG. 11 coupled to a cap and a swivel elbow, according to one embodiment.

FIG. 12 illustrates a side view of the barrel 120 of FIG. 1 coupled to a cap 1102 and a swivel elbow 1104, according to one embodiment. The barrel 120 to cap 1102 connection may be facilitated with a high-pitched thread. For example, the thread may be six thread per inch double start right-hand thread. Because of the double start, the effective pitch becomes 0.333", meaning that for every half revolution of the cap 1102, the linear movement equals 0.333". In some embodiments, the length of the threads on the barrel 120 may be 0.47" long. Therefore, when the cap 1102 is engaged with the barrel 120, the user can rotate the cap 1102 a total of 1.4 revolutions (0.47"+0.333"=1.4) before it hits a hard stop. Various other thread pitches are likewise within the scope of this disclosure, including effective pitches from 0.1" to 0.4", including from 0.15" to 0.25".

The barrel 120 to swivel elbow 1104 connection may also be facilitated with a high-pitched thread. For example, a six thread per inch double start right-hand thread may be used. In some embodiments, the length of the threads on the barrel 120 may be 0.367" long (0.693"−0.326"=0.367"). Therefore, when the swivel elbow 1104 is engaged with the barrel 120, the user can rotate the swivel elbow 1104 a total of 1.1 revolutions (0.367"+0.333"=1.1) before it hits a hard stop. Various other thread pitches are likewise within the scope of this disclosure, including effective pitches from 0.1" to 0.4", including from 0.15" to 0.25".

When compared with a typical thread, a very small amount of rotation couples the devices to the barrel 120. Having these rapid connections on the proximal and distal ends of the barrel 120 may provide an ergonomic, quick and user-friendly assembly, improving the user's experience with the system.

Figure 13:
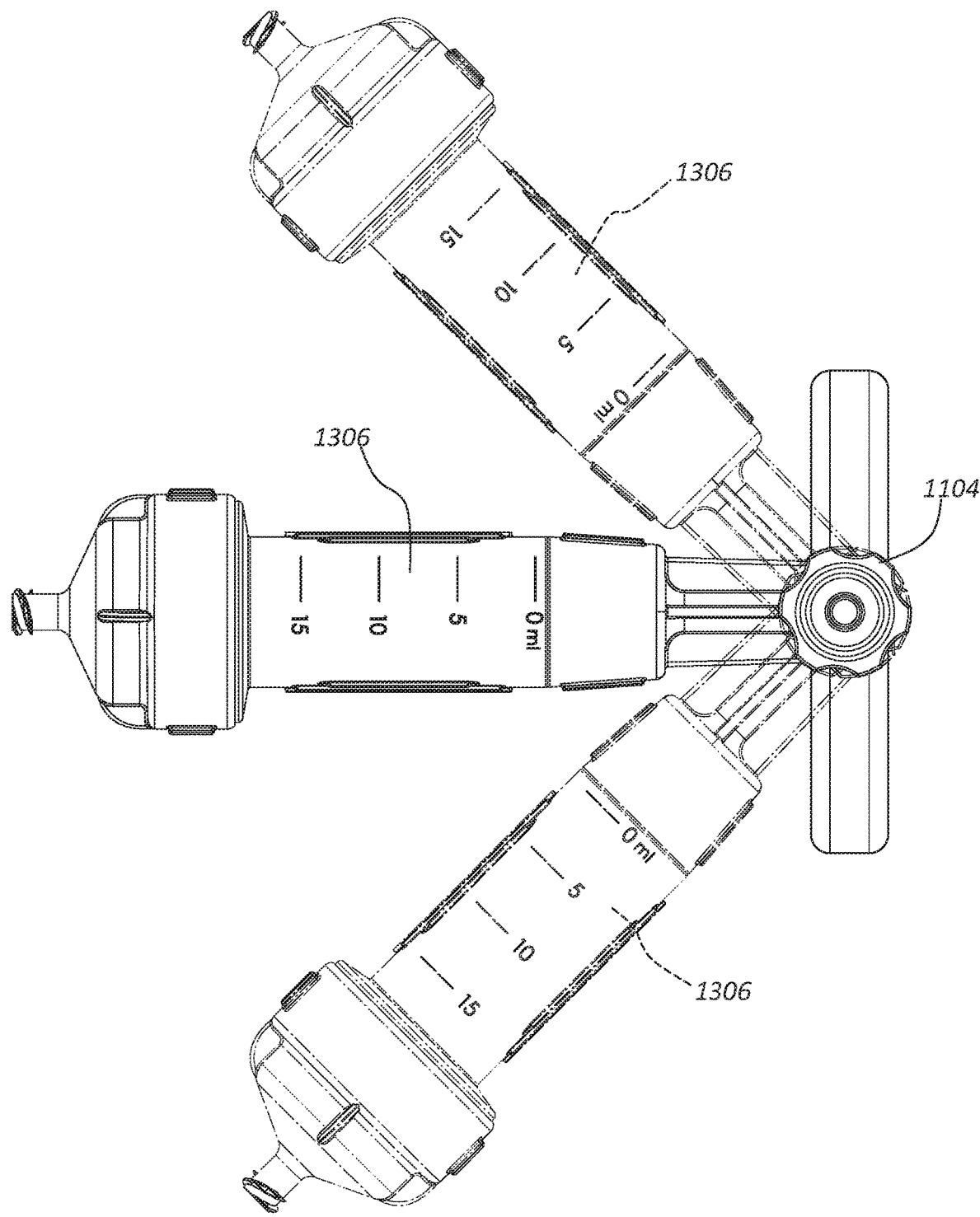
FIG. 13 illustrates a graduated barrel that may be used as disclosed with reference to FIG. 1.

FIG. 13 illustrates a graduated barrel 1306 that may be used as analogously to the barrel 120 of FIG. 1 and the drawings and disclosure related to the barrel 120. The graduated barrel 1306 may be made of a transparent material (providing visibility to the plunger and cement inside). In some embodiments, the graduated barrel 1306 may be marked with precise graduations in 1 cc increments enabling the clinician to accurately monitor the volume of cement delivered.

As shown, the graduated barrel 1306 may rotate around the swivel elbow 1104, allowing a practitioner to manipulate the position of the graduated barrel 1306 for better imaging or convenience. The rotatability allows a practitioner to optimize visibility during the procedure. In some embodiments, the swivel elbow 1104 allows the graduated barrel 1306 to rotate 360 degrees around a delivery needle.

Figure 14:
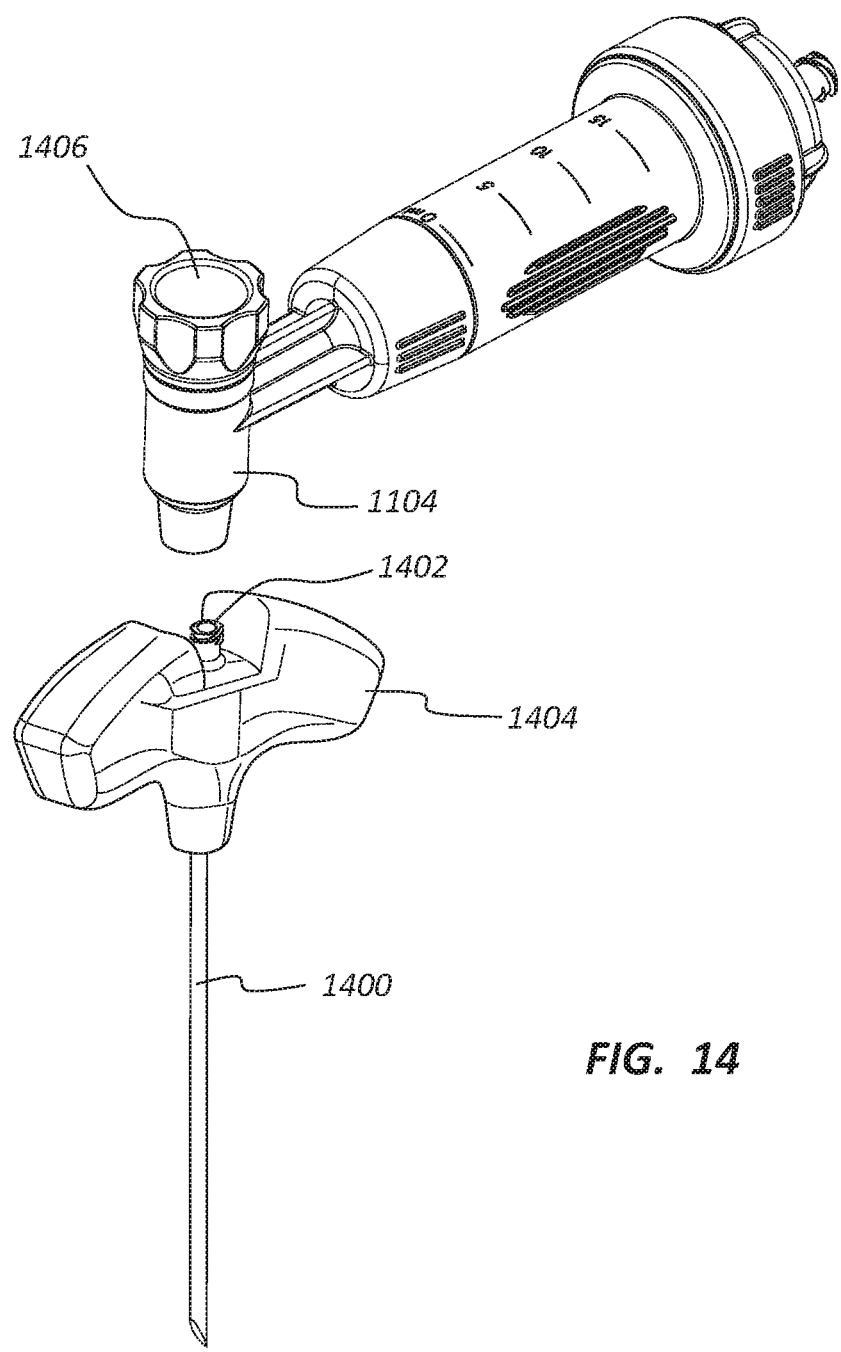
FIG. 14 illustrates the multi-interface syringe of FIG. 1 configured to couple to a delivery syringe via a swivel elbow, according to one embodiment.

FIG. 14 illustrates the multi-interface syringe 100 of FIG. 1 configured to couple to a delivery needle 1400 via the swivel elbow 1104, according to one embodiment. A luer connector 1402 of the delivery needle 1400 may be recessed in the contour of the delivery needle handle 1404 making it challenging to connect to. A thumb knob 1406 on the swivel elbow 1104 may rotate separately from the multi-interface syringe 100 and be used to tighten the luer connection between the delivery needle handle 1404 and the swivel elbow 1104, providing a more accessible tightening mechanism.

Figure 15:
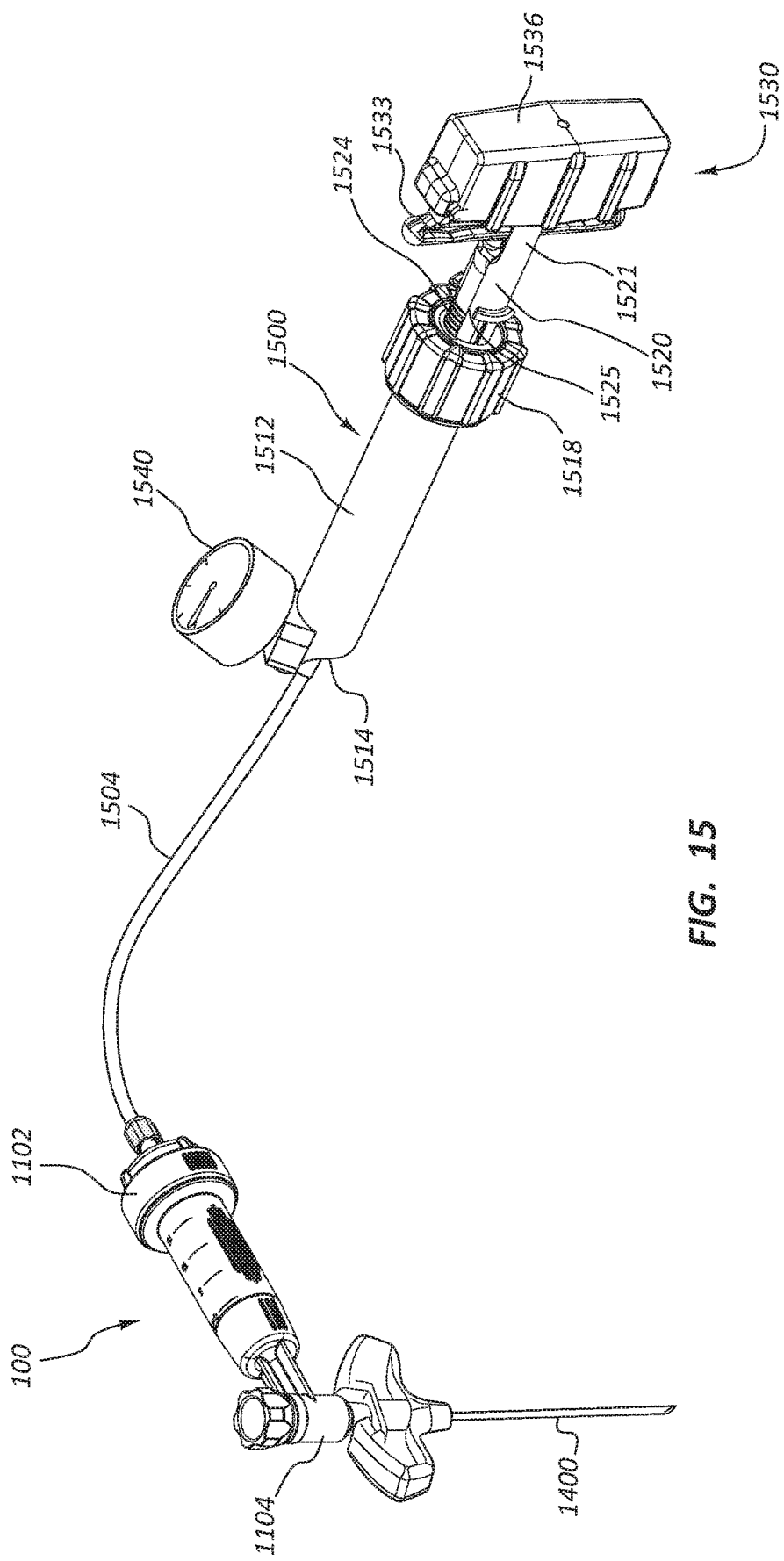
FIG. 15 illustrates a perspective view of the multi-interface syringe of FIG. 1 coupled to a pressure delivery device and a delivery needle.

FIG. 15 illustrates a perspective view of the multi-interface syringe 100 of FIG. 1 coupled to a pressure delivery device 1500 and the delivery needle 1400. To reduce obstruction for imaging of the delivery site, the swivel elbow 1104 may rotate to manipulate the position of the multi-interface syringe 100. Further, the practitioner may control the delivery from a distance due to the length of tubing 1504 coupling the multi-interface syringe 100 and the pressure delivery device 1500.

As the cement cures, the viscosity of the cement increases which may make it hard to deliver. The pressure delivery device 1500 may provide sufficient force to deliver the cement. In some embodiments, the pressure delivery device 1500 may pressurize a gas or liquid in the tubing 1504. The pressure may force the plunger within the multi-interface syringe 100 to move toward the swivel elbow 1104. As the plunger moves, the cement may flow through the delivery needle 1400 to the delivery site.

As shown, the pressure delivery device 1500 may couple to the multi-interface syringe 100 via the cap 1102. The cap 1102 may have a standard luer interface to adapt the proximal opening of the multi-interface syringe 100 to a standard interface. The tubing 1504 between the multi-interface syringe 100 and the pressure delivery device 1500 may be flexible to reduce the effect of a practitioner's movement on the rotational position of the multi-interface syringe 100.

The pressure delivery device 1500 may comprise a syringe body 1512, a plunger 1520, and a handle 1530. The syringe body 1512 may be formed of a generally cylindrical hollow tube configured to receive the plunger 1520. The syringe body 1512 may include an inlet/outlet port coupled to the tubing 1504. In some embodiments, a nut 1518 may be coupled to the syringe body 1512 adjacent a proximal end of the syringe body 1512. The nut 1518 may include a center hole configured to allow the plunger 1520 to pass through the nut 1518 into the syringe body 1512. Further, the nut 1518 may include internal nut threads configured to selectively couple the nut 1518 to the plunger 1520 in some embodiments.

The plunger 1520 may be configured to be longitudinally displaceable within the syringe body 1512. The plunger 1520 may comprise of a plunger shaft 1521 coupled to a plunger seal at the distal end of the plunger shaft 1521. The plunger shaft 1521 may also be coupled to the handle 1530 at the proximal end of the plunger shaft 1521, the plunger shaft 1521 spanning the distance between the plunger seal and the handle 1530.

The handle 1530 broadly refers to the group of components coupled to the proximal end of the plunger 1520, some of which may be configured to be graspable by a user. In certain embodiments, the handle 1530 may be configured such that the user may manipulate the position of the plunger 1520 by manipulating the handle 1530. Further, in some embodiments the handle 1530 may be an actuator mechanism, configured to manipulate components of the pressure delivery device 1500.

A fluid reservoir may be defined by the space enclosed by the inside walls of the syringe body 1512 between the plunger seal and the distal end 1514 of the syringe body 1512. Accordingly, movement of the plunger seal with respect to the syringe body 1512 will alter the size and volume of the fluid reservoir. The pressure delivery device 1500 may further include a pressure gauge 1540 to measure the pressure as the plunger seal moves.

The nut 1518 may utilize threads or other coupling mechanisms to couple the nut 1518 to the syringe body 1512. The nut 1518 may additionally include internal nut threads configured to couple the nut 1518 to a portion of the plunger 1520. The plunger 1520 may also include external plunger threads 1525 configured to couple the plunger 1520 to the nut 1518. The plunger 1520 may thus be translated longitudinally with respect to the syringe body 1512 by rotating the plunger 1520 such that the interaction of the nut threads and the plunger threads 1525 results in the longitudinal translation of the plunger 1520. Thus, when the plunger threads 1525 and internal nut threads are engaged, movement of the plunger 1520 is constrained with respect to the syringe body 1512, though the plunger 1520 is not necessarily fixed with respect to the syringe body 1512. For example, the plunger 1520 may be rotatable, but not directly translatable, when the plunger threads 1525 are engaged.

The plunger threads 1525 may be configured such that they may be retracted within the plunger shaft 1521. For example, the plunger threads 1525 may be formed on a thread rail 1524 which may be disposed within a groove in the plunger shaft 1521. In some embodiments, translation of the thread rail 1524 in the proximal direction simultaneously causes the thread rail 1524 to retract toward the center axis of the plunger shaft 1521. Similarly, translation of the thread rail 1524 in the distal direction may cause the thread rail 1524 to move away from the center axis of the plunger shaft 1521.

In the illustrated embodiment, a distally oriented biasing force acting on the thread rail 1524 may bias the plunger threads 1525 to the non-retracted position. It will be appreciated by one of ordinary skill in the art having the benefit of this disclosure that it is within the scope of this disclosure to modify the angles and interfaces such that a distally oriented biasing force on the thread rail 1524 would bias the plunger threads 1525 in the retracted position. When the thread rail 1524 is disposed in a non-retracted position, the plunger threads 1525 are engaged with the internal nut threads. When the thread rail 1524 is sufficiently retracted into the plunger shaft 1521, the plunger threads 1525 are not engaged with the internal nut threads.

Embodiments which utilize retractable threads may allow a user to displace the plunger shaft 1521 relative to the syringe body 1512 either through rotation of the plunger shaft 1521 (and the subsequent interaction of threads), or by retracting the plunger threads 1525 and displacing the plunger shaft 1521 by applying opposing forces on the plunger shaft 1521 and the syringe body 1512. (The forces, of course, may move the plunger shaft 1521 distally or proximally with respect to the syringe body 1512.) Both methods of displacement may be utilized during the course of a single therapy.

Quick displacement of the plunger shaft 1521 may be accomplished by retracting the plunger threads 1525 and sliding the plunger shaft 1521 relative to the syringe body 1512. For example, a practitioner may quickly fill the reservoir with fluid by disengaging the plunger threads 1525 and pulling the plunger shaft 1521 in a proximal direction with respect to the syringe body 1512. Further, a practitioner may quickly force fluid into lines leading to other devices or quickly expel unwanted air bubbles from the reservoir by retracting the plunger threads 1525 and repositioning the plunger shaft 1521.

In other instances, the practitioner may desire more precise control over the position of the plunger shaft 1521 (for example when displacing the plunger shaft 1521 in order to adjust the fluid pressure within the reservoir) or it may simply be difficult or impossible without a mechanical advantage to displace the plunger shaft 1521 due to high fluid pressure within the reservoir. For example, as the viscosity of the cement increases additional pressure may need to be applied. In these instances, the practitioner may opt to displace the plunger shaft 1521 by rotation of the plunger shaft 1521.

The handle 1530 of the pressure delivery device 1500 may include components which enable a practitioner to retract the thread rail 1524 of the plunger 1520. In some embodiments, the plunger shaft 1521 may be fixed to a first member such as an inner member of the handle 1530. The thread rail 1524 may be fixed to a trigger 1533 component of the handle 1530. Further, a biasing component may be configured to bias the trigger 1533 in a distal direction. Because the trigger 1533 is fixed to the thread rail 1524, a distally oriented force on the trigger 1533 will result in a distally oriented force on the thread rail 1524 as well. The force provided by the biasing component may thus bias the thread rail 1524 in a non-retracted position as described above. Conversely, overcoming the biasing force and translating the trigger 1533 in a proximal direction with respect to the plunger shaft 1521 and an inner member may retract the plunger threads 1525.

In some embodiments the handle 1530 may further include a second member such as an outer sleeve 1536 and one or more levers. The levers may be disposed such that they provide a mechanical advantage, enabling the user to more easily overcome the biasing force and draw the trigger 1533 toward the inner member.

The pressure delivery device 1500 may allow a practitioner precise control when delivering bone cement to a delivery site. For example, when delivering cement into the vertebral body, the practitioner needs to determine when to stop the flow for a safe and effective treatment. Because the pressure delivery device 1500 is driving the cement, the practitioner may pull the trigger 1533 to release the threads to instantaneously stop the flow of cement. Other systems may require a counter rotation of the plunger handle or manual withdrawal of the plunger to stop cement delivery. In contrast, the trigger 1533 results in immediate depressurization and there is no need to withdraw the plunger 1520.

Figure 16:
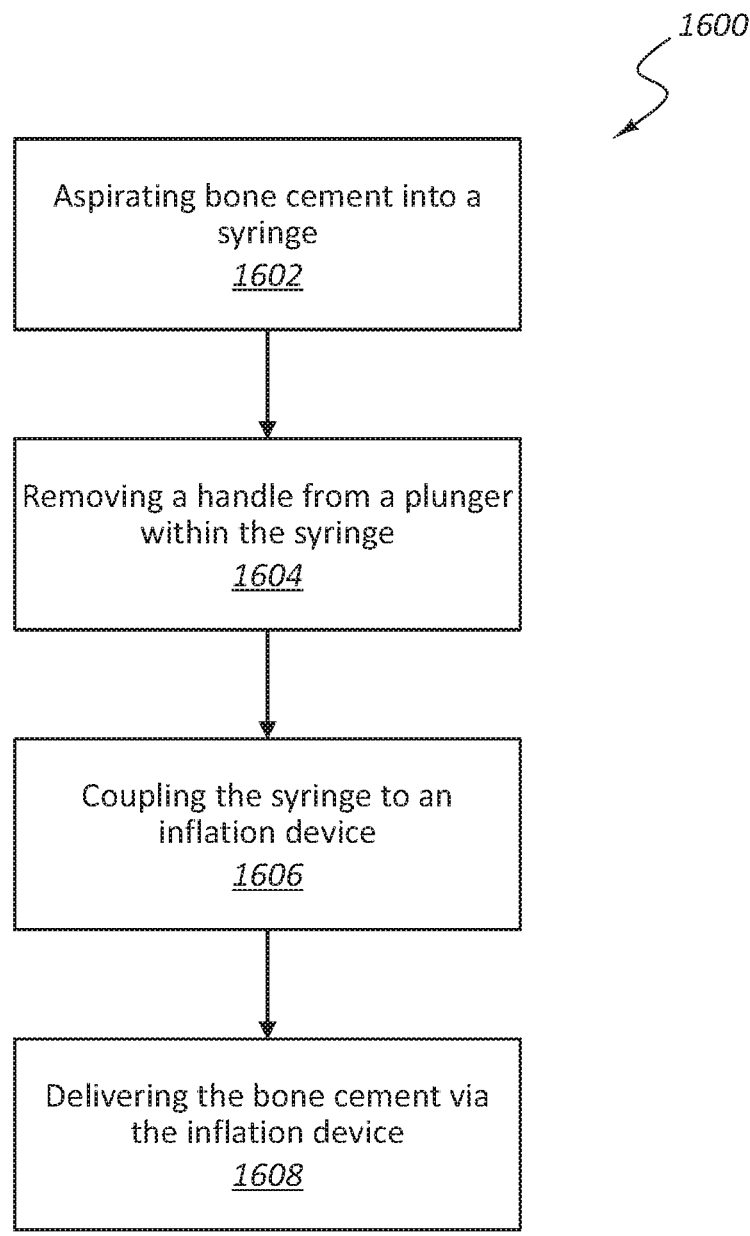
FIG. 16 is a flow chart of a method for delivering bone cement.

FIG. 16 is a flow chart of a method 1600 for delivering bone cement. A practitioner may aspirate 1602 bone cement into a syringe by pulling a handle coupled to a plunger within the syringe. The practitioner may remove 1604 the handle from the plunger within the syringe by applying a rotational force to the handle. The practitioner may couple 1606 the syringe to a pressure delivery device. The practitioner may also couple the syringe to a cement delivery needle, cannula, swivel elbow, or other component. The practitioner may deliver 1608 the bone cement from the syringe to the patient by applying a pressure to the plunger via the pressure delivery device.

Figure 17:
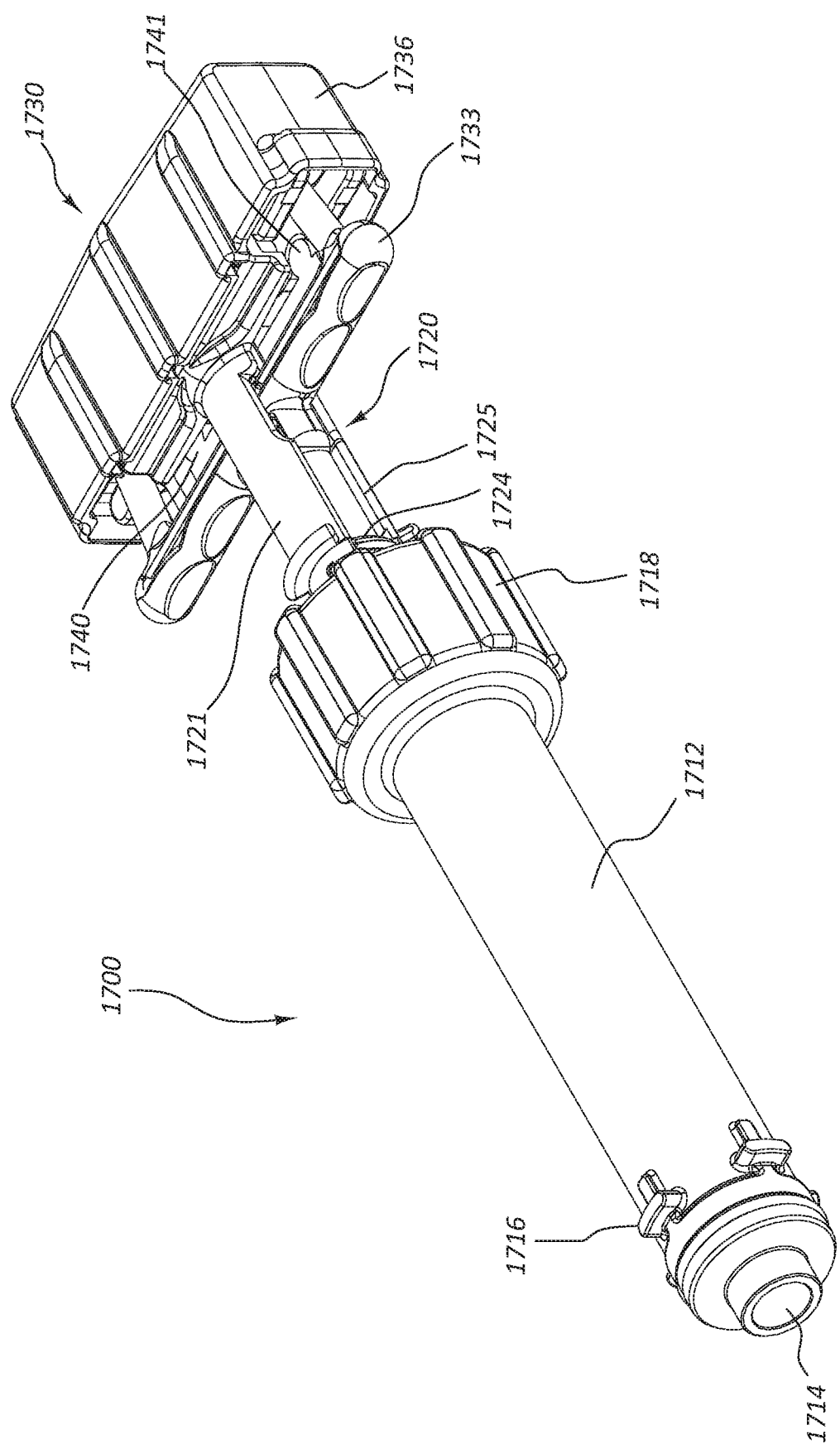
FIG. 17 illustrates a perspective view of a high-pressure cement delivery syringe (high-pressure syringe), according to one embodiment.

FIG. 17 illustrates a perspective view of a high-pressure cement delivery syringe (high-pressure syringe) 1700, according to one embodiment. The high-pressure syringe 1700 may include the features found on the pressure delivery device 1500 of FIG. 15. For instance, the high-pressure syringe 1700 may include a syringe body 1712, a plunger 1720, and a handle 1730.

The syringe body 1712 may include a nut 1718 with internal nut threads configured to selectively couple the nut 1718 to the plunger 1720. The plunger 1720 may include plunger threads 1725 to couple to the internal nut threads. The plunger threads 1725 may be configured such that they may be retracted within a plunger shaft 1721. For example, the plunger threads 1725 may be formed on a thread rail 1724 which may be disposed within a groove in the plunger shaft 1721.

Embodiments which utilize retractable threads may allow a user to displace the plunger shaft 1721 relative to the syringe body 1712 either through rotation of the plunger shaft 1721 (and the subsequent interaction of threads), or by retracting the plunger threads 1725 and displacing the plunger shaft 1721 by applying opposing forces on the plunger shaft 1721 and the syringe body 1712. (The forces, of course, may move the plunger shaft 1721 distally or proximally with respect to the syringe body 1712.) Both methods of displacement may be utilized during the course of a single therapy.

The handle 1730 of the high-pressure syringe 1700 may include components which enable a practitioner to retract the thread rail 1724 of the plunger 1720. For instance, a practitioner may apply a force to a trigger 1733. The trigger 1733 may cause the thread rail 1724 to retract as discussed with reference to FIG. 15. In some embodiments the handle 1730 may further include a second member such as an outer sleeve 1736 and one or more levers 1740, 1741. The levers 1740, 1741 may be disposed such that they provide mechanical advantage, enabling the user to more easily overcome the biasing force and actuate the trigger 1733.

Additionally, the high-pressure syringe 1700 may include features to directly aspirate bone cement into the syringe body 1712, and features to deliver bone cement stored in the syringe body 1712 to the delivery site. For instance, the high-pressure syringe 1700 may include a tapered nose 1714 to aspirate cement from a mixing system as described with reference to FIG. 18. Further, the high-pressure syringe 1700 may include mating features 1716 to adapt the tapered nose 1714 to couple to a delivery system as described with reference to FIGS. 19-21. Further, the syringe body 1712 may be molded in a material known to tolerate the caustic effects of the monomer used to create the cement.

Figure 18:
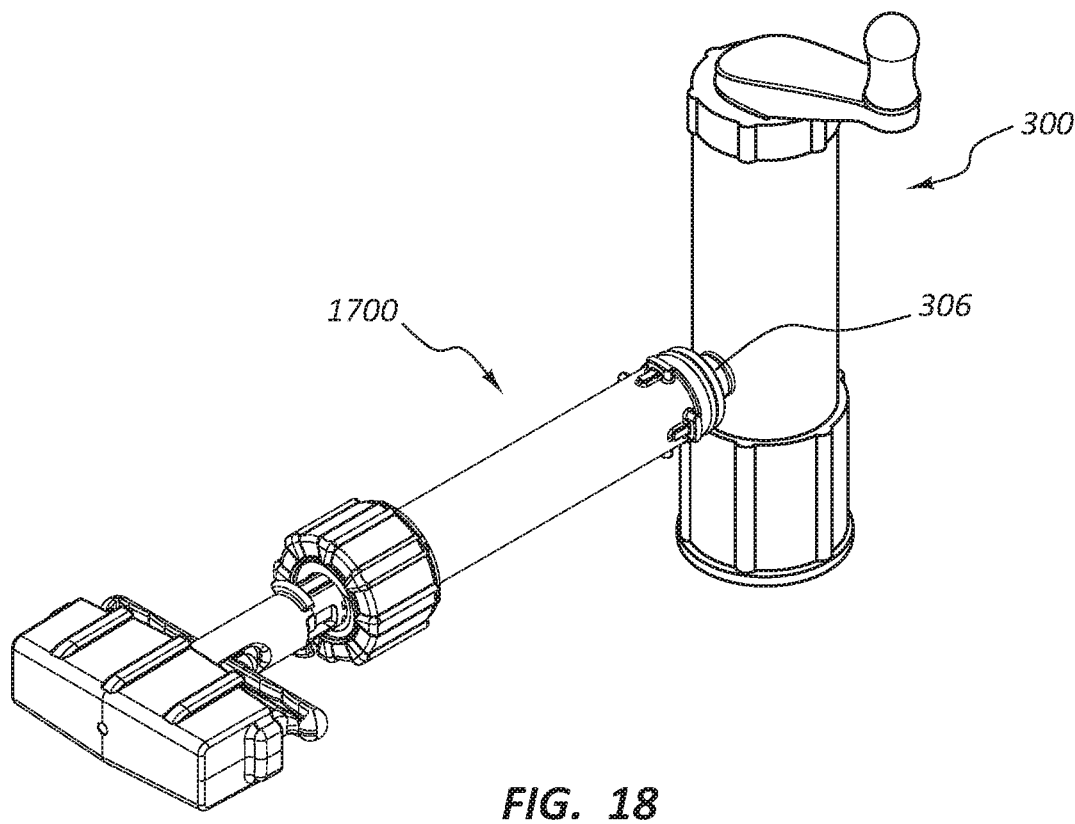
FIG. 18 illustrates a perspective view of the high-pressure syringe of FIG. 17 interfacing with a mixing system.

FIG. 18 illustrates a perspective view of the high-pressure syringe 1700 of FIG. 17 interfacing with a mixing system 300. The mixing system 300 may be used as described with reference to FIG. 3. The shape of the tapered nose and the side port 306 provide a snug interference fit. The interference fit prevents cement from escaping while a practitioner uses the high-pressure syringe 1700 to aspirate the cement with the floor in a lowered position. Cement may be drawn into the barrel by drawing back on the handle.

Figure 19A:
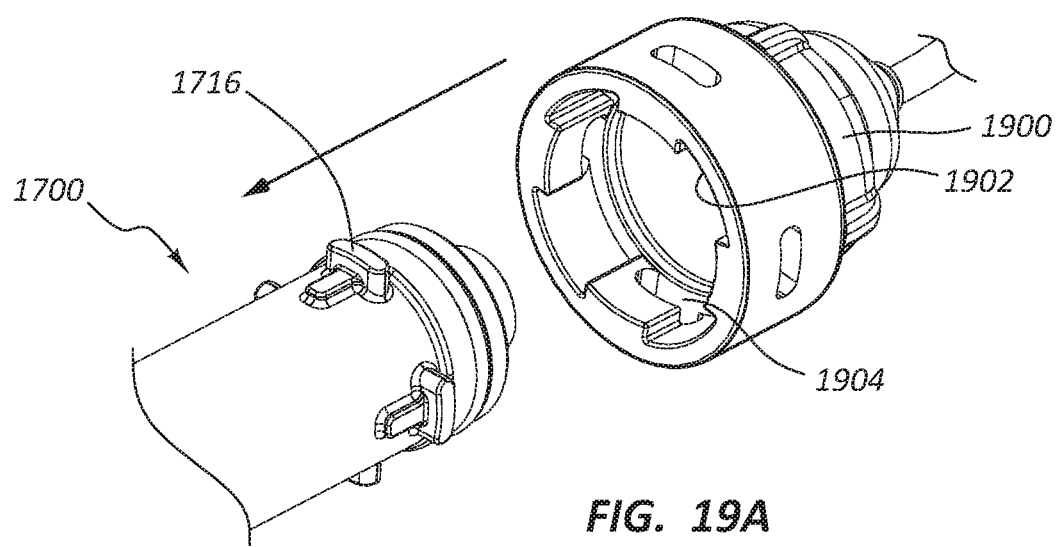
FIG. 19A illustrates a perspective view of the high-pressure syringe of FIG. 17 aligned with a quick connect cap.
Figure 19B:
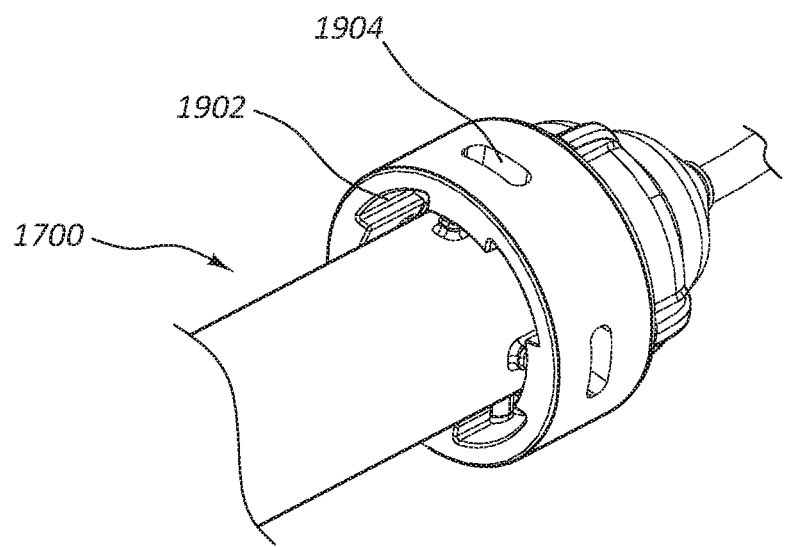
FIG. 19B illustrates a perspective view of the high-pressure syringe of FIG. 17 coupled with the quick connect cap.

FIGS. 19A and 19B illustrate a quick connect cap 1900 coupling process. Specifically, FIG. 19A illustrates a perspective view of the high-pressure syringe 1700 of FIG. 17 aligned with a quick connect cap 1900. The quick connect cap 1900 may provide an interface between the high-pressure syringe 1700 and a delivery needle. The quick connect cap 1900 may contain mating features (e.g., 1902, 1904) corresponding to the mating features 1716 of the high-pressure syringe 1700. As shown, the mating features 1902, 1904 of the quick connect cap 1900 may include receiving slots 1902 and catches 1904. The receiving slots 1902 may facilitate placement of the quick connect cap 1900 on the high-pressure syringe 1700.

FIG. 19B illustrates a perspective view of the high-pressure syringe 1700 of FIG. 17 coupled with the quick connect cap 1900. As shown, the quick connect cap 1900 may be rotated on the distal end of the high-pressure syringe 1700. The mating features 1716 of the high-pressure syringe 1700 may be retained by the catches 1904 to secure the quick connect cap 1900. In some embodiments the quick connect cap 1900 and the high-pressure syringe 1700 may interface via threads.

Figure 20:
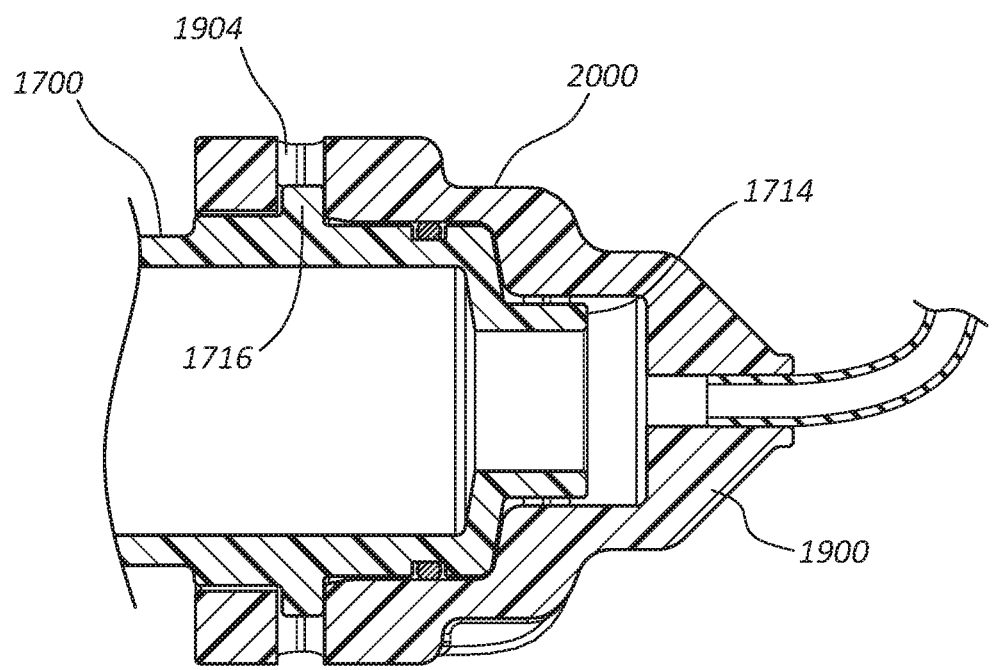
FIG. 20 illustrates a cross-section of the quick connect cap of FIGS. 19A and 19B locked into position to deliver cement.

FIG. 20 illustrates a cross-section of the quick connect cap 1900 of FIGS. 19A and 19B locked into position to deliver cement. As shown, the mating features 1716 of the high-pressure syringe 1700 are retained within the catches 1904 of the quick connect cap 1900. This interlocks the two components together. A seal may prevent cement flowing from the tapered nose 1714 from leaking.

Figure 21:
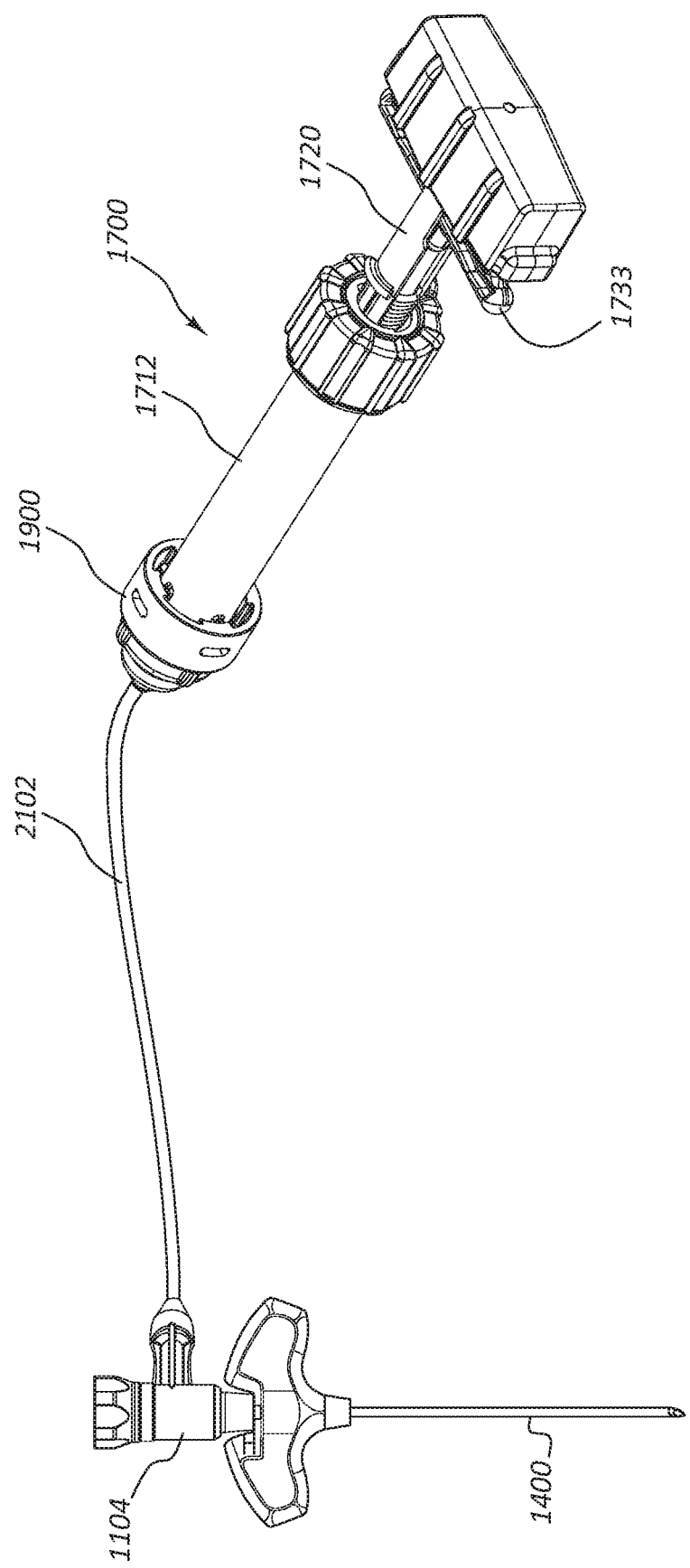
FIG. 21 illustrates a perspective view of the high-pressure syringe of FIG. 17 coupled with a delivery needle.

FIG. 21 illustrates a perspective view of the high-pressure syringe 1700 of FIG. 17 coupled with a delivery needle 1400. As shown, the quick connect cap 1900 may couple the high-pressure syringe 1700 to a swivel elbow 1104 coupled to the delivery needle 1400. In one embodiment, the quick connect cap 1900 may be pre-connected to a length of flexible tubing 2102 (approximately two to three feet) to provide a practitioner with ample separation from x-ray radiation while the delivery site is being imaged. On the distal end of the flexible tubing 2102 may be a pre-connected swivel elbow 1104 which would be connected by the practitioner to the delivery needle 1400 positioned in a delivery site such as a fractured vertebra.

The quick-release facilitated by the trigger 1733 and the retractable threads provide precise control over delivery of bone cement stored in the syringe body 1712. For example, when delivering cement into the vertebral body, the practitioner needs to determine when to stop the flow for a safe and effective treatment. Because the high-pressure syringe 1700 is driving the cement, the practitioner may pull the trigger 1733 to release the threads to instantaneously stop the flow of cement. Other systems may require a counter rotation of the plunger handle or manual withdrawal of the plunger to stop cement delivery. In contrast, the trigger 1733 results in immediate depressurization and there is no need to withdraw the plunger 1720.

Figure 22:
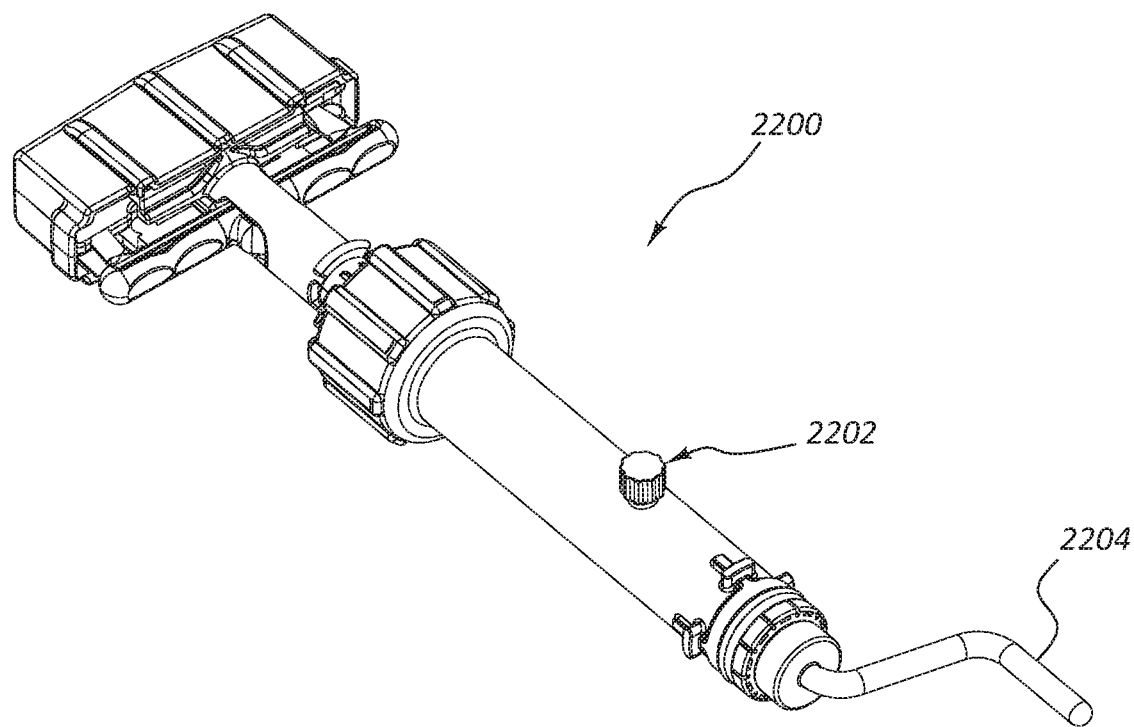
FIG. 22 illustrates a perspective view of a high-pressure syringe with an internal mixing apparatus to mix bone cement within the syringe.

FIG. 22 illustrates a perspective view of a high-pressure syringe 2200 with an internal mixing apparatus 2204 to mix bone cement within the high-pressure syringe 2200. The features of the high-pressure syringe 2200 correspond to those described with reference to the high-pressure syringe 1700 of FIG. 17 with an additional side port 2202 and the internal mixing apparatus 2204. Therefore, all the features disclosed with reference to the high-pressure syringe 1700 of FIG. 17 apply to the high-pressure syringe 2200. While the internal mixing apparatus 2204 is shown in the high-pressure syringe 2200, the internal mixing apparatus 2204 may be used in some embodiments of the multi-interface syringe 100 of FIG. 1.

Figure 23:
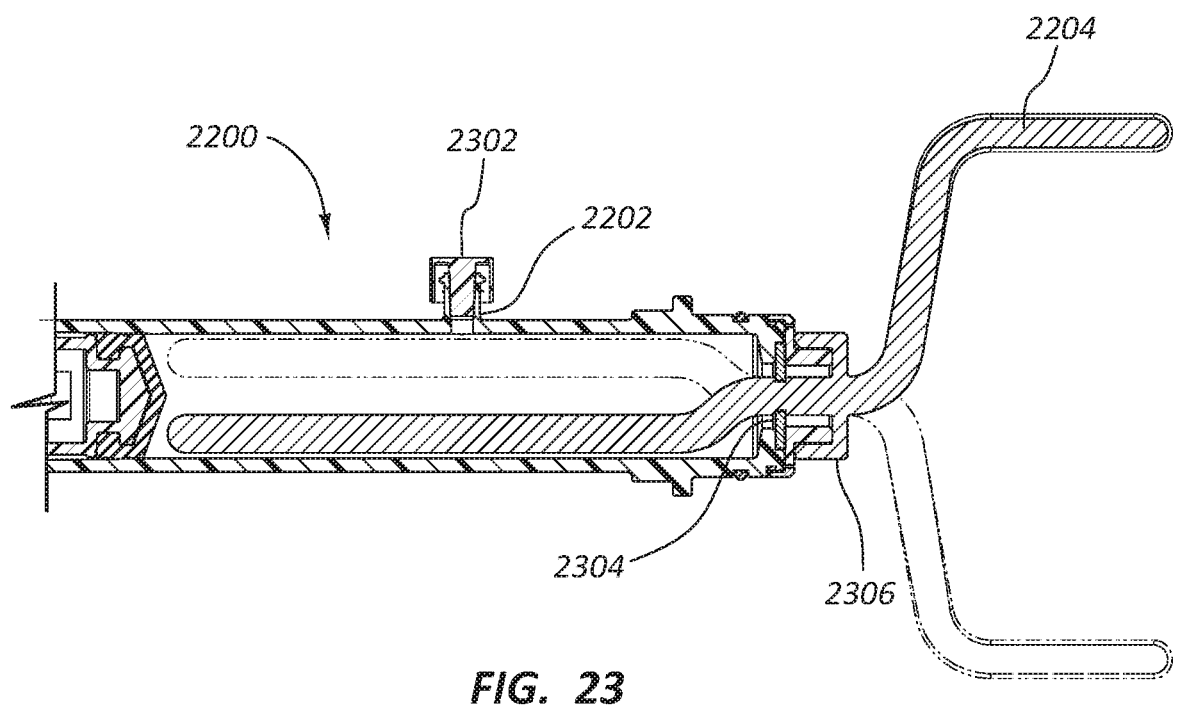
FIG. 23 illustrates a cross-sectional view of the high-pressure syringe with the internal mixing apparatus of FIG. 22.

FIG. 23 illustrates a cross-sectional view of the high-pressure syringe 2200 with the internal mixing apparatus 2204 of FIG. 22. In some embodiments, dry powder cement may be pre-loaded in the high-pressure syringe 2200. The mixing apparatus 2204 may be contained within the high-pressure syringe 2200 with the powder. The side port 2202 may include a luer fitting and a cap 2302 that selectively blocks the side port 2202.

As shown, the mixing apparatus 2204 may include a rod with a handle protruding from the high-pressure syringe 2200. The mixing apparatus 2204 may be selectively coupled to the high-pressure syringe 2200 via a retaining cap 2306. The retaining cap 2306 may have a snap fit, threaded interface, pin, or other locking interface to secure the retaining cap 2306 to the high-pressure syringe 2200.

A seal 2304 may prevent cement from escaping the high-pressure syringe 2200 while the mixing apparatus 2204 is inserted. The seal 2304 may be coupled to a distal end of the high-pressure syringe 2200. The seal 2304 may also wipe the cement from the mixing apparatus 2204 when the mixing apparatus 2204 is removed from the high-pressure syringe 2200.

Figure 24:
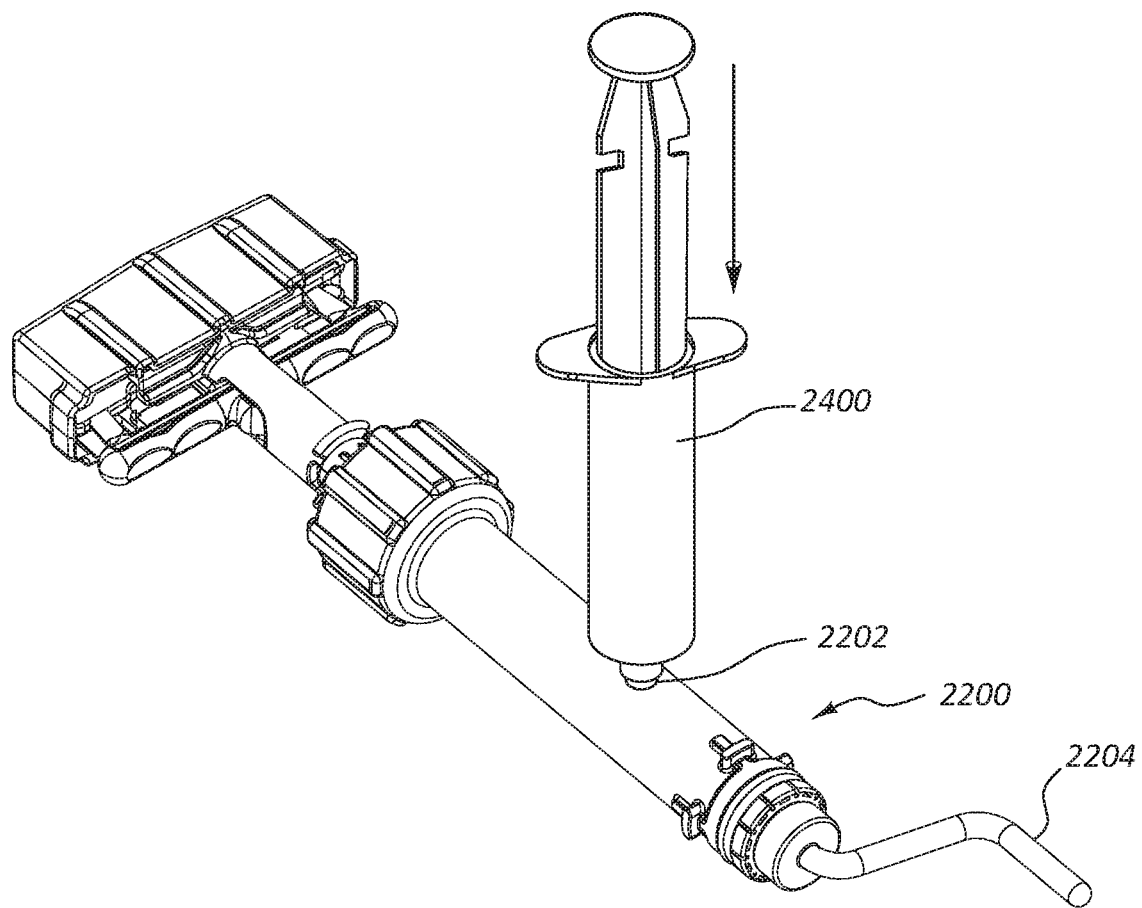
FIG. 24 illustrates a perspective view of the high-pressure syringe with the internal mixing apparatus of FIG. 22 coupled with a syringe to load a monomer, according to one embodiment.

FIG. 24 illustrates a perspective view of the high-pressure syringe 2200 with the mixing apparatus 2204 of FIG. 22 coupled with a syringe 2400 to load a monomer, according to one embodiment. A practitioner may remove the cap from the side port 2202 and connect the syringe 2400 loaded with the monomer. In the illustrated embodiment, the practitioner may pour the monomer into the syringe 2400. In some embodiments, the monomer may be provided in a self-contained syringe. In some embodiments, a practitioner may perform some action to ready the syringe 2400 for injection. For example, the practitioner may break an ampule open inside the syringe 2400.

Figure 25:
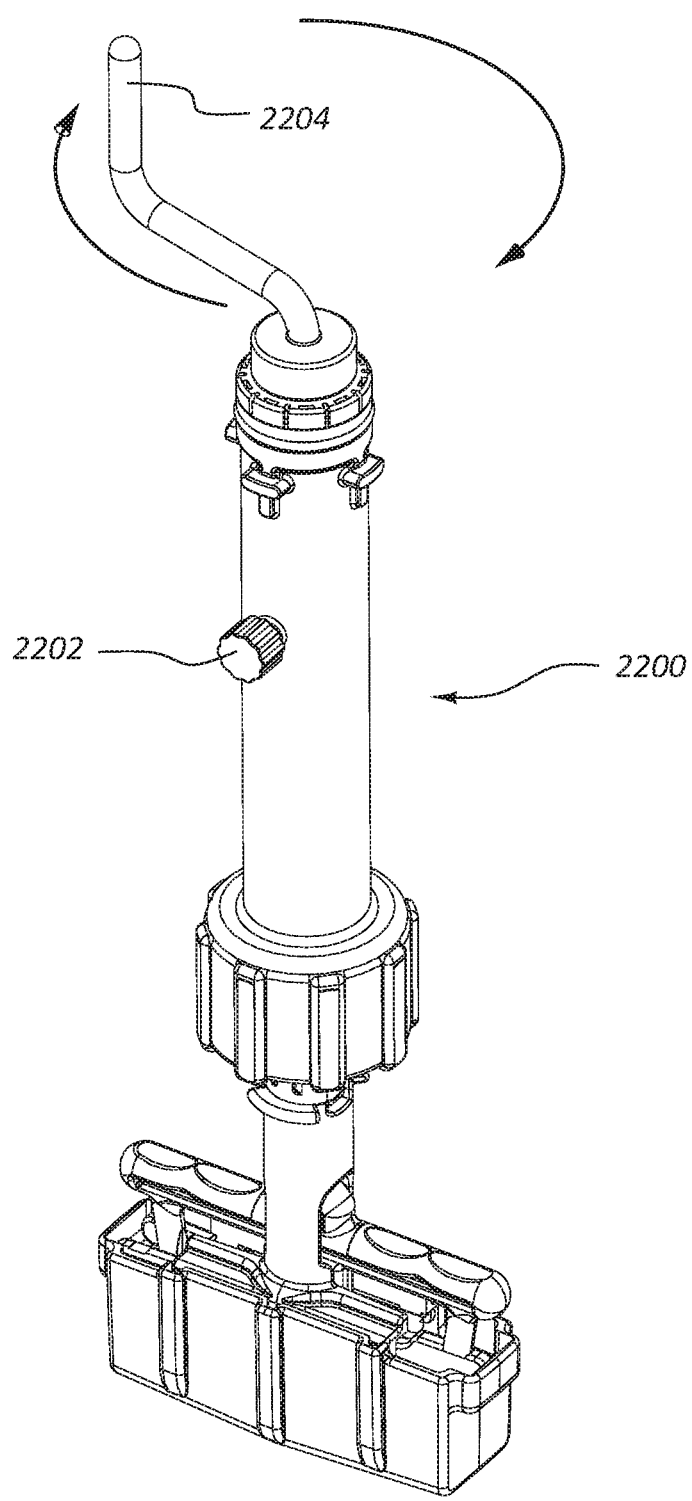
FIG. 25 illustrates a perspective view of the internal mixing apparatus rotating in the high-pressure syringe of FIG. 22.

FIG. 25 illustrates a perspective view of the internal mixing apparatus 2204 rotating in the high-pressure syringe 2200 of FIG. 22. In some embodiment, once the liquid monomer is inside the high-pressure syringe 2200, a practitioner may replace the cap on the side port 2202 and rotate the mixing apparatus 2204. For example, in one embodiment, a practitioner may is rotate the mixing apparatus 2204 for approximately one minute (or other designated time frame) to combine the liquid monomer with the bone cement powder stored in the high-pressure syringe 2200.

Figure 26:
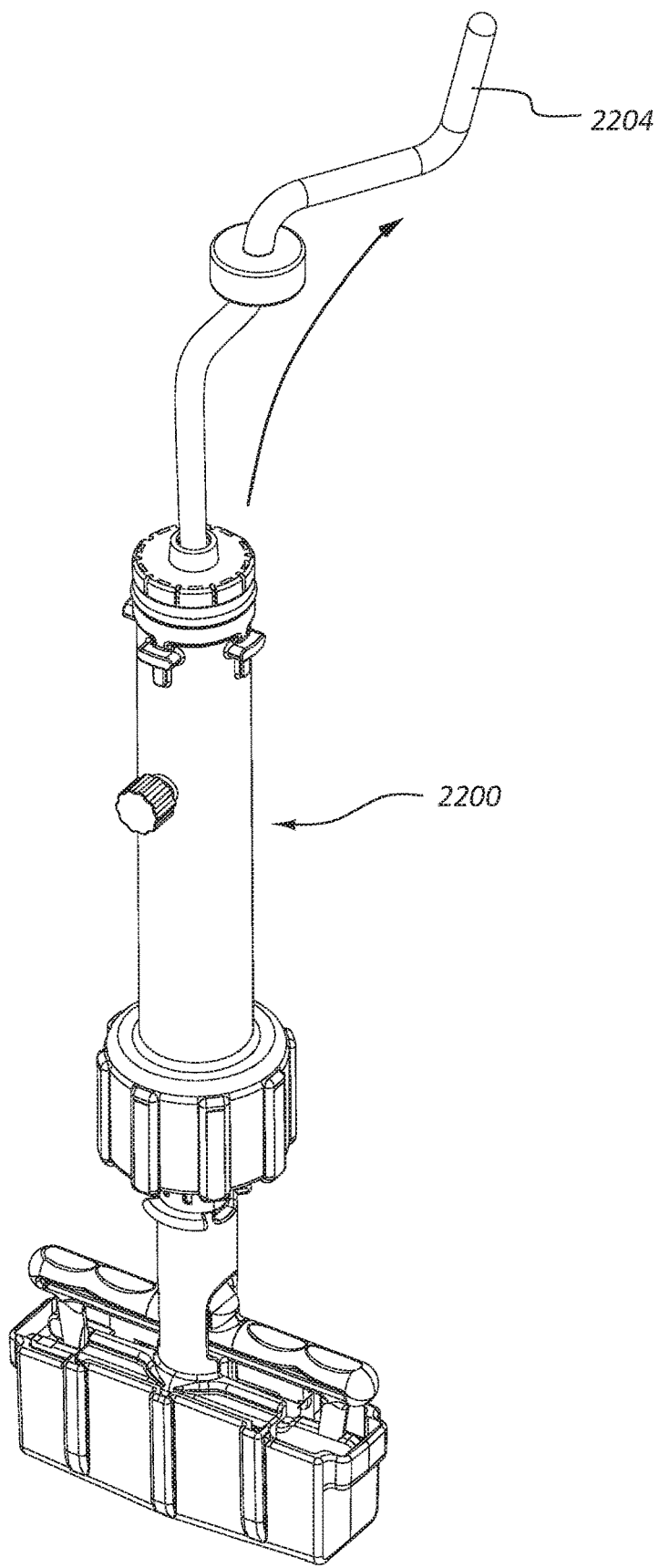
FIG. 26 illustrates a perspective view of the internal mixing apparatus being removed from the high-pressure syringe of FIG. 22.

FIG. 26 illustrates a perspective view of the internal mixing apparatus 2204 being removed from the high-pressure syringe 2200 of FIG. 22. Once the cement powder and the liquid monomer are combined, a practitioner may remove the mixing rod 2204 from the high-pressure syringe 2200. As the mixing rod 2204 is pulled from the high-pressure syringe 2200 a built-in seal/wiper cleans the cement from the mixing rod 2204.

Figure 27A:
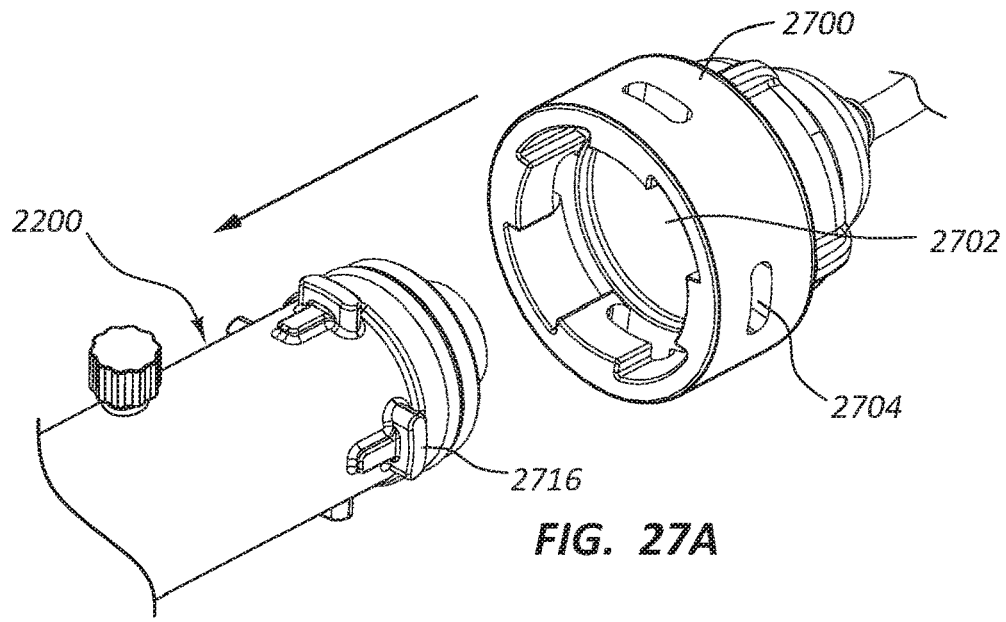
FIG. 27A illustrates a perspective view of the high-pressure syringe of FIG. 22 aligned with a quick connect cap.
Figure 27B:
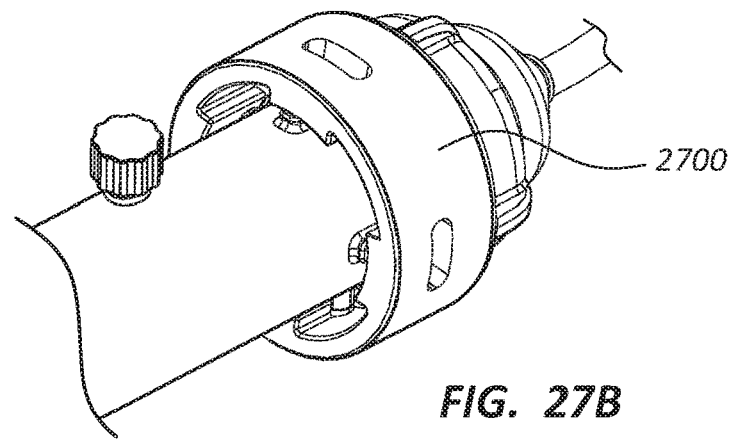
FIG. 27B illustrates a perspective view of the high-pressure syringe of FIG. 22 coupled with the quick connect cap.
Figure 27C:
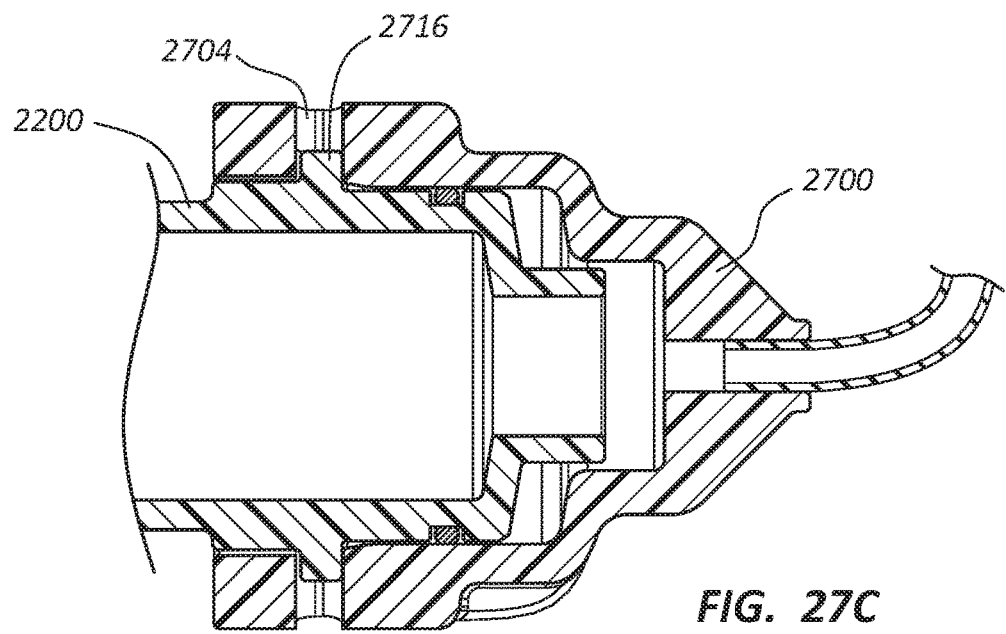
FIG. 27C illustrates a cross-section of the quick connect cap of FIGS. 27A and 27B locked into position to deliver cement.

FIGS. 27A-27C illustrate a quick connect cap 2700 coupling process. Specifically, FIG. 27A illustrates a perspective view of the high-pressure syringe 2200 of FIG. 22 aligned with a quick connect cap 2700. The quick connect cap 2700 may provide an interface between the high-pressure syringe 2200 and a delivery needle. The quick connect cap 2700 may contain mating features (e.g., 2702, 2704) corresponding to the mating features 2216 of the high-pressure syringe 2200. As shown, the mating features 2702, 2704 of the quick connect cap 2700 may include receiving slots 2702 and catches 2704. The receiving slots 2702 may facilitate placement of the quick connect cap 2700 on the high-pressure syringe 2200.

FIG. 27B illustrates a perspective view of the high-pressure syringe 2200 of FIG. 22 coupled with the quick connect cap 2700. As shown, the quick connect cap 2700 may be rotated on the distal end of the high-pressure syringe 2200. Mating features 2716 of the high-pressure syringe 2200 may be retained by the catches 2704 to secure the quick connect cap 2700. In some embodiments the quick connect cap 2700 and the high-pressure syringe 2200 may interface via threads.

FIG. 27C illustrates a cross-section of the quick connect cap 2700 of FIGS. 27A and 27B locked into position to deliver cement. As shown, the mating features 2716 of the high-pressure syringe 2200 are retained within the catches 2704 of the quick connect cap 2700. This interlocks the two components together. A seal may prevent cement flowing from leaking.

Figure 28:
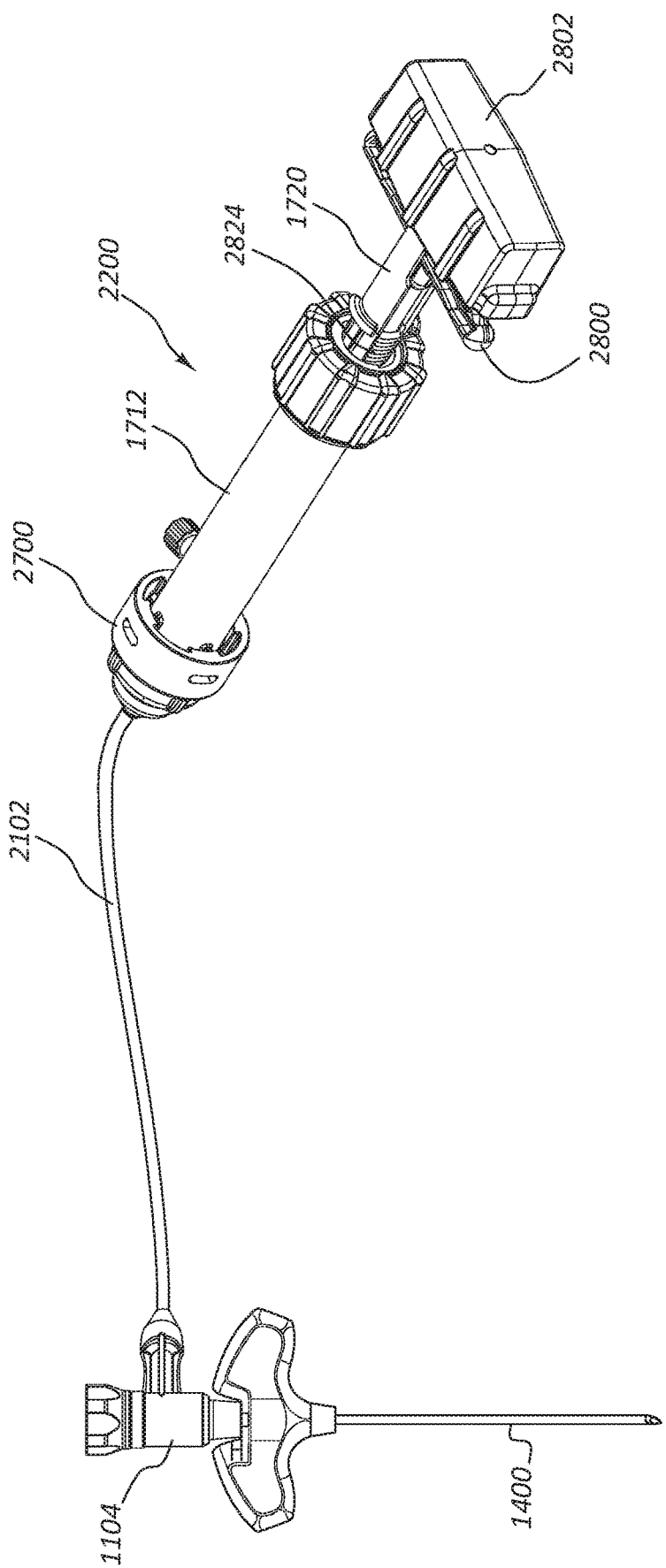
FIG. 28 illustrates a perspective view of the high-pressure syringe of FIG. 22 coupled with a delivery needle.

FIG. 28 illustrates a perspective view of the high-pressure syringe 2200 of FIG. 22 coupled with the delivery needle 1400. As shown, the quick connect cap 2700 may couple the high-pressure syringe 2200 to a swivel elbow 1104 coupled to the delivery needle 1400. In one embodiment, the quick connect cap 2700 may be pre-connected to a length of flexible tubing 2102 (approximately two to three feet) to provide a practitioner with ample separation from x-ray radiation while the delivery site is being imaged. On the distal end of the flexible tubing 2102 may be a pre-connected swivel elbow 1104 which would be connected by the practitioner to the delivery needle 1400 positioned in a delivery site such as a fractured vertebra.

A quick-release may provide precise control over delivery of bone cement stored in the syringe body 1712. A practitioner may depress a trigger 2800 in a handle 2802 to implement the quick release. For example, when delivering cement into the vertebral body, the practitioner may determine when to stop the flow for a safe and effective treatment and pull the trigger 2800. When the practitioner pulls the trigger 2800 a set of threads 2824 coupling the plunger 1720 in place may retract. Because the high-pressure delivery syringe 2200 is driving the cement, depressing the trigger 2800 results in immediate depressurization, stopping the flow of cement.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A system for mixing and delivering a fluid treatment to a patient, the system comprising:
    a mixer to mix the fluid treatment prior to delivery, the mixer comprising:
        a mixing chamber; and
        a port to facilitate access to the mixing chamber;
    a syringe to extract the fluid treatment from the mixer and deliver the extracted fluid treatment to a patient, the syringe comprising:
        a barrel to hold the fluid treatment, the barrel including a distal nose to interface with the port;
        a plunger within the barrel to displace the fluid treatment;
        a handle selectively coupled to the plunger to facilitate plunger movement; and
        a retainer removeably attachable to a proximal end of the barrel, wherein the retainer engages the plunger when the plunger is positioned at the proximal end and prevents the plunger from rotating relative to the barrel; and
    a pressure delivery device to selectively couple to the syringe when the handle is removed from the plunger, wherein the pressure delivery device pressurizes the syringe to facilitate plunger movement,
    wherein the retainer comprises a socket with a mating surface corresponding to a mating proximal portion of the plunger, and
    wherein the mating surface of the socket engages with the mating proximal portion of the plunger to prevent rotational movement of the plunger relative to the barrel.

2. The system of claim 1, wherein the mixer further comprises a paddle within the mixing chamber coupled to a handle exterior of the mixing chamber, wherein a rotation of the handle of the mixer causes the paddle to stir bone cement powder and a liquid monomer within the mixing chamber.

3. The system of claim 1, wherein the mixer further comprises a floor configured to selectively move from a first position to a second position, wherein when in the first position the floor seals the port, and when in the second position the port is open.

4. The system of claim 1, wherein the handle comprises a set of arms at a distal end, the set of arms positioned around a longitudinal axis of the handle and configured to flex toward the longitudinal axis of the handle when the handle is rotated relative to the plunger so as to facilitate removal of the handle from the plunger.

5. The system of claim 1, further comprising an adapter to selectively couple to the syringe when the handle is removed from the plunger, the adapter comprising an interface to couple the pressure delivery device to the syringe.

6. The system of claim 1, further comprising a swivel elbow to selectively couple the distal nose of the barrel to a delivery needle.

7. The system of claim 1, wherein the plunger comprises a seal.

8. The system of claim 1, wherein the mating proximal portion comprises multiple facets disposed around an axis of the plunger.

9. The system of claim 1, wherein the mating surface comprises multiple facets disposed around an axis of the retainer.

10. The system of claim 1, wherein the handle comprises a handgrip and an elongate shaft selectively coupled to the plunger to facilitate plunger movement relative to the barrel, and
    wherein the handle is configured to release from the plunger when the mating proximal portion is coupled with the mating surface and the handle is rotated relative to the plunger.

11. The system of claim 1, wherein the mating surface is tapered in a longitudinal direction of the barrel, and
    wherein the mating proximal portion is tapered in a longitudinal direction of the barrel.

12. A system for delivering a fluid treatment to a patient, the system comprising:
    a syringe comprising:
        a barrel to hold the fluid treatment, the barrel including a distal nose;
        a plunger within the barrel to displace the fluid treatment;
        a handle selectively coupled to the plunger to facilitate plunger movement; and
        a retainer removeably attachable to a proximal end of the barrel, the retainer comprising a socket with a mating surface corresponding to a mating proximal portion of the plunger,
    wherein when the plunger is positioned at the proximal end the mating surface of the socket engages with the mating proximal portion of the plunger to prevent rotational movement of the plunger relative to the barrel.

13. The system of claim 12, wherein the handle comprises a set of arms at a distal end, the set of arms positioned around a longitudinal axis of the handle and configured to flex toward the longitudinal axis of the handle when the handle is rotated relative to the plunger so as to facilitate removal of the handle from the plunger.

14. The system of claim 12, wherein the mating proximal portion comprises multiple facets disposed around an axis of the plunger.

15. The system of claim 12, wherein the mating surface comprises multiple facets disposed around an axis of the retainer.

16. The system of claim 12, wherein the handle is configured to release from the plunger when the mating proximal portion is coupled with the mating surface and the handle is rotated relative to the plunger.

17. The system of claim 12, further comprising an adapter to selectively couple to the syringe when the handle is removed from the plunger, the adapter comprising an interface to couple a pressure delivery device to the syringe.

18. A system for delivering a fluid treatment to a patient, the system comprising:
    a syringe comprising:

a barrel to hold the fluid treatment, the barrel including a distal nose;

a plunger within the barrel to displace the fluid treatment; and a handle selectively coupled to the plunger to facilitate plunger movement, the handle comprising a set of arms at a distal end, the set of arms positioned around a longitudinal axis of the handle and configured to flex toward the longitudinal axis of the handle when the handle is rotated relative to the plunger so as to facilitate removal of the handle from the plunger.

19. The system of claim 18, wherein the syringe further comprises a retainer removeably attachable to a proximal end of the barrel, the retainer comprising a socket with a mating surface corresponding to a mating proximal portion of the plunger, wherein when the plunger is positioned at the proximal end the mating surface of the socket engages with the mating proximal portion of the plunger to prevent rotational movement of the plunger relative to the barrel.

* * * * *

UNITED STATES PATENT AND TRADEMARK OFFICE
CERTIFICATE OF CORRECTION

PATENT NO. : 11,304,739 B2
APPLICATION NO. : 16/053011
DATED : April 19, 2022
INVENTOR(S) : Purdy et al.

It is certified that error appears in the above-identified patent and that said Letters Patent is hereby corrected as shown below:

On the Title Page

Line 66, under Related U.S. Application Data reads, "Substitute for Application..." which should read, "Provisional application ...."

Signed and Sealed this
Twenty-first Day of November, 2023

Katherine Kelly Vidal
*Director of the United States Patent and Trademark Office*